(12) United States Patent
Chakilam et al.

(10) Patent No.: US 10,544,107 B2
(45) Date of Patent: Jan. 28, 2020

(54) PROCESS FOR THE PREPARATION OF 2-{4-[(5,6-DIPHENYL PYRAZIN-2-YL)(ISOPROPYL)AMINO]BUTOXY}-N-(METHYLSULFONYL)ACETAMIDE AND NOVEL POLYMORPHS THEREOF

(71) Applicants: MAITHRI DRUGS PRIVATE LIMITED, Telangana (IN); Nagaraju Chakilam, Telangana (IN); Kondana Ramprasad Achampeta, Telangana (IN); Pradeep Rebelli, Telangana (IN); Tavitayya Kondaka, Telangana (IN)

(72) Inventors: Nagaraju Chakilam, Telangana (IN); Kondana Ramprasad Achampeta, Telangana (IN); Pradeep Rebelli, Telangana (IN); Tavitayya Kondaka, Telangana (IN)

(73) Assignee: MAITHRI DRUGS PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 16/315,671

(22) PCT Filed: Jun. 30, 2017

(86) PCT No.: PCT/IN2017/000108
§ 371 (c)(1),
(2) Date: Jan. 7, 2019

(87) PCT Pub. No.: WO2018/008042
PCT Pub. Date: Jan. 11, 2018

(65) Prior Publication Data
US 2019/0152927 A1    May 23, 2019

(30) Foreign Application Priority Data

Jul. 5, 2016   (IN) .............................. 201641023049
Jul. 22, 2016  (IN) .............................. 201641025120
Mar. 17, 2017  (IN) .............................. 201741009226

(51) Int. Cl.
*C07D 241/20*   (2006.01)
*B01D 9/00*     (2006.01)
*A61P 9/12*     (2006.01)

(52) U.S. Cl.
CPC ........... *C07D 241/20* (2013.01); *B01D 9/005* (2013.01); *A61P 9/12* (2018.01)

(58) Field of Classification Search
CPC .......... A61P 9/12; B01D 9/005; C07D 241/20
See application file for complete search history.

(56) References Cited

U.S. PATENT DOCUMENTS 7,205,302 B2 *  4/2007  Asaki ................. A61K 31/4418
                                                514/241
8,791,122 B2    7/2014  Itou

OTHER PUBLICATIONS

Caira Mino R. et. al, Crystalline Polymorphism of Organic Compounds, Topics in Current Chemistry, Design of Organic Solids, Springer, (Jan. 1, 1998), Abstract, 1 page.
International Search Report (ISR; PCT/ISA/210), dated Oct. 23, 2017, 5 pages.
Written Opinion of the International Seaching Authority; dated Oct. 23, 2017, 6 pages.

* cited by examiner

*Primary Examiner* — Alexander R Pagano
*Assistant Examiner* — Ebenezer O Sackey
(74) *Attorney, Agent, or Firm* — IP Pundit LLC

(57) ABSTRACT

The present invention relates to a processes for the preparation of 2-{4-[(5,6-diphenyl pyrazin-2-yl)(isopropyl)amino]butoxy}-N-(methylsulfonyl)acetamide compound of formula-1 and novel polymorphs thereof.

18 Claims, 6 Drawing Sheets

PROCESS FOR THE PREPARATION OF 2-{4-[(5,6-DIPHENYL PYRAZIN-2-YL)(ISOPROPYL)AMINO]BUTOXY}-N-(METHYLSULFONYL)ACETAMIDE AND NOVEL POLYMORPHS THEREOF

RELATED APPLICATIONS

This application claims the benefit of Indian patent application numbers 201641023049 filed on 5 Jul. 2016, 201641025120 filed on 22 Jul. 2016 and 201741009226 filed on 17 Mar. 2017 which are incorporated herein reference.

FIELD OF THE INVENTION

The present invention relates to an improved and novel processes for the preparation of 2-{4-[(5,6-diphenylpyrazin-2-yl)(isopropyl)amino]butoxy}-N-(methylsulfonyl) acetamide compound of formula-1, which is represented by the following structural formula-1.

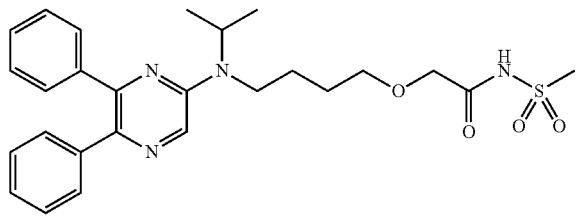

Formula-1

The present invention also relates to novel crystalline forms of the compound of formula-1 and process for the preparation thereof.

BACKGROUND OF THE INVENTION

2-{4-[(5,6-diphenylpyrazin-2-yl)(isopropyl)amino]butoxy}-N-(methylsulfonyl) acetamide is known as Selexipag. It is developed by Nippon Shinyaku under the brand name of Uptravi®, for the treatment of pulmonary arterial hypertension.

2-{4-[(5,6-diphenylpyrazin-2-yl)(isopropyl)amino]butoxy}-N-(methylsulfonyl) acetamide was firstly described in U.S. Pat. No. 7,205,302B2 herein after referred as US'302. The said patent also describes its process for the preparation. According to this process the final product was obtained with low yield and purity.

U.S. Pat. No. 8,791,122 (herein after referred as US'122) patent describes crystalline form-I, II and III of 2-{4-[(5,6-diphenylpyrazin-2-yl)(isopropyl)amino]butoxy}-N-(methylsulfonyl) acetamide. Because of drug compounds having, for example, improved stability, solubility, shelf life and in vivo pharmacology, are consistently sought, there is an ongoing need for new or pure salts, hydrates, solvates and polymorphic forms of existing drug molecules. The novel crystalline forms of 2-{4-[(5,6-diphenylpyrazin-2-yl)(isopropyl)amino]butoxy}-N-(methylsulfonyl) acetamide described herein help meet this requirement.

US'122 patent describes amorphous form of the compound of formula-1. This patent does not disclose any detailed process for amorphous form and PXRD pattern of amorphous compound of formula-1.

The present invention provides an improved process for the preparation of amorphous form of the compound of formula-1.

The prior art processes described for the preparation of the compound of formula-1 suffer from drawbacks such as more no of steps with low yield and purity. Hence there is a continuous need to develop an improved and novel process for preparation for the compound of formula-1 for commercial manufacturing with high yields and purity.

The present invention describes novel and improved process for the preparation of the compound of formula-1 over the existing processes. The invention also provides novel crystalline forms of the compound of formula-1 and its process for the preparation thereof.

BRIEF DESCRIPTION

The first aspect of the present invention is to provide an improved process for the preparation of 2-{4-[(5,6-diphenylpyrazin-2-yl)(isopropyl)amino]butoxy}-N-(methyl sulfonyl) acetamide the compound of formula-1.

The second aspect of the present invention is to provide an improved process for the preparation of the compound of formula-1.

The third aspect of the present invention is to provide an improved process for the preparation of the compound of formula-4.

The fourth aspect of the present invention is to provide an improved process for the preparation of the compound of formula-1.

The fifth aspect of the present invention is to provide novel process for the preparation of the compound of formula-6.

The sixth aspect of the present invention is to provide novel process for the preparation of the compound of formula-1.

The seventh aspect of the present invention is to provide novel process for the preparation of the compound of formula-1.

The eighth aspect of the present invention is to provide compound of formula-12.

The ninth aspect of the present invention is to provide an improved process for the preparation of the compound of general formula-5.

The tenth aspect of the present invention is to provide an improved process for the preparation of the compound of formula-1.

The eleventh aspect of the present invention is to provide novel crystalline form of 2-{4-[(5,6-diphenylpyrazin-2-yl)(isopropyl)amino]butoxy}-N-(methylsulfonyl)acetamide compound of formula-1, herein after designated as crystalline form-P.

The twelfth aspect of the present invention is to provide a process for the preparation of crystalline form-P of 2-{4-[(5,6-diphenylpyrazin-2-yl)(isopropyl)amino]butoxy}-N-(methyl sulfonyl) acetamide compound of formula-1.

The thirteenth aspect of the present invention is to provide novel crystalline form of 2-{4-[(5,6-diphenylpyrazin-2-yl)(isopropyl)amino]butoxy}-N-(methylsulfonyl)acetamide compound of formula-1, herein after designated as crystalline form-L.

The fourteenth aspect of the present invention is to provide a process for the preparation of form-L of 2-{4-[(5,6-diphenylpyrazin-2-yl)(isopropyl)amino]butoxy}-N-(methylsulfonyl) acetamide compound of formula-1.

The fifteenth aspect of the present invention is to provide novel crystalline form of 2-{4-[(5,6-diphenylpyrazin-2-yl)

(isopropyl)amino]butoxy}-N-(methylsulfonyl) acetamide, herein after designated as crystalline form-M.

The sixteenth aspect of the present invention is to provide a process for the preparation of form-M of 2-{4-[(5,6-diphenylpyrazin-2-yl)(isopropyl)amino]butoxy}-N-(methylsulfonyl) acetamide compound of formula-1.

The seventeenth aspect of the present invention is to provide crystalline form-D of 2-{4-[(5,6-diphenylpyrazin-2-yl)(isopropyl)amino]butoxy}-N-(methyl sulfonyl) acetamide compound of formula-1 and its process for the preparation thereof.

The eighteenth aspect of the present invention is to provide a process for the preparation of an amorphous form of 2-{4-[(5,6-diphenylpyrazin-2-yl)(isopropyl) amino]butoxy}-N-(methyl sulfonyl) acetamide compound of formula-1.

DETAILED DESCRIPTION

Figure 1:
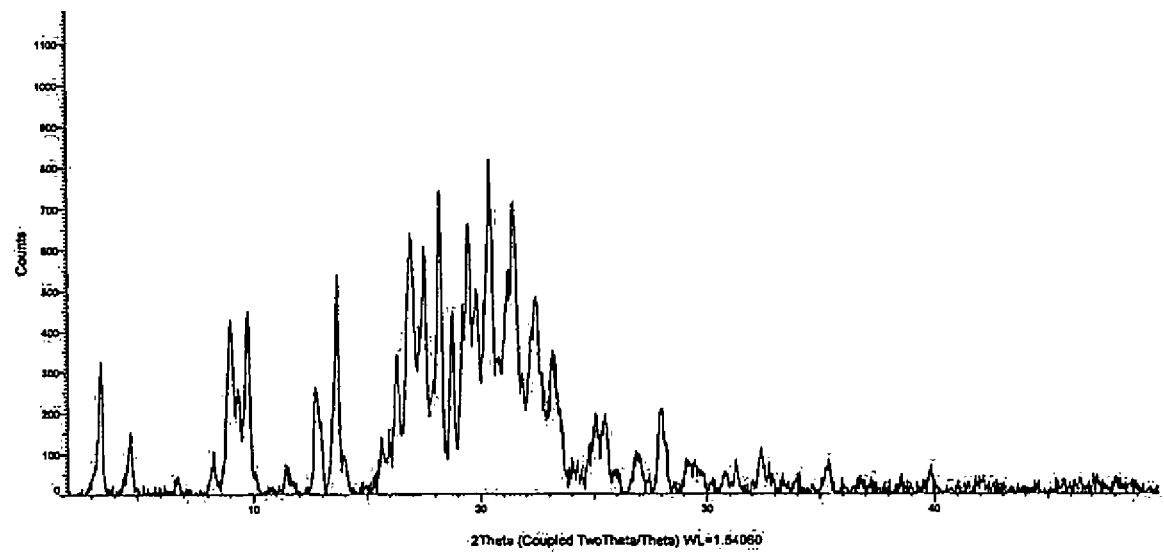
FIG. 1: Illustrates the PXRD pattern of crystalline form-M of 2-{4-[(5,6-diphenylpyrazin-2-yl) (isopropyl) amino]butoxy}-N-(methylsulfonyl) acetamide compound of formula-1.

As used herein the term "suitable solvent" used in the present invention refers to "hydrocarbon solvents" such as n-hexane, n-heptane, cyclohexane, pet ether, toluene, pentane, cycloheptane, methyl cyclohexane, m-, o-, or p-xylene and the like; "ether solvents" such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethylsulfoxide (DMSO), N-methylpyrrolidone (NMP) and the like; "chloro solvents" such as dichloromethane, dichloroethane, chloroform, carbontetra chloride and the like; "ketone solvents" such as acetone, methyl ethyl ketone, methyl isobutyl ketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

As used herein the present invention the term "suitable base" refers to inorganic or organic base. Inorganic base refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropyl amine, diisopropylethylamine, diisobutylamine, triethylamine, pyridine, 4-dimethylamino pyridine (DMAP), N-methyl morpholine (NMM), 2,6-lutidine, lithium diisopropylamide; organo silicon bases such as lithium hexamethyldisilazide (LiHMDS), sodium hexamethyldisilazide (NaHMDS), potassium hexamethyldisilazide (KHMDS) or mixtures thereof.

The term "acid" used in the present invention refers to inorganic acids selected from hydrochloric acid, hydrobromic acid, sulfuric acid, nitric acid, phosphoric acid etc; organic acids such as acetic acid, maleic acid, malic acid, tartaric acid, oxalic acid, trifluoroacetic acid, methane sulfonic acid, p-toluene sulfonic acid etc.; Lewis acids and like.

The term "coupling agent" used in the present invention is selected form N,N'-dicyclohexylcarbodiimide (DCC), N,N'-diisopropylcarbodiimide (DIC), carbonyldiimidazole (CDI), 1-ethyl-3-(3-dimethylaminopropyl)carbodiimide hydrochloride (EDC.HCl), O-(7-aza-benzotriazole-1-yl)-N,N,N',N'-tetramethyl uronium hexafluoro phosphate (HATU), alkyl or aryl chloroformates such as ethyl chloroformate, benzylchloroformate, diphenylphosphoroazidate (DPPA), thionyl chloride, pivalyl chloride, oxalyl chloride, phosphorous oxychloride, phosphorous pentachloride, 4-methyl-2-oxopentanoyl chloride (i-BuCOCOCl), benzotriazol-1-yl-oxytripyrrolidino phosphonium hexafluorophosphate (PyBOP), methane sulfonyl chloride and the like; optionally in combination with 1-hydroxy-7-azatriazole (HOAt), 1-hydroxy benzotriazole (HOBt), 1-hydroxy-1H-1,2,3-triazole-4-carboxylate (HOCt), O-(benzotriazol-1-yl)-N,N,N',N'-tetramethyluronium tetrafluoroborate (TBTU), N-hydroxysuccinamide (HOSu), N-hydroxysulfosuccinimide (Sulfo-NHS), 4-dimethylaminopyridine (DMAP).

The first aspect of the present invention provides an improved process for the preparation of 2-{4-[(5,6-diphenylpyrazin-2-yl)(isopropyl)amino]butoxy}-N-(methylsulfonyl) acetamide compound of formula-1,

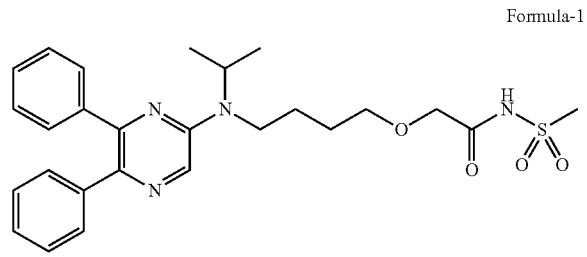 [SMILES: CC(C)N(CCCCOCC(=O)NS(C)(=O)=O)c1cnc(-c2ccccc2)c(-c2ccccc2)n1]

Formula-1 comprising of:
a) Reacting the compound of formula-2

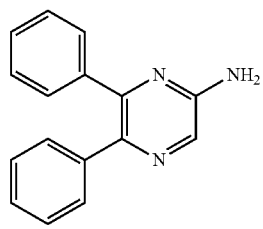

Formula-2 with the compound of general formula-3

Formula-3 wherein X is a leaving group such as halogen, mesyloxy or tosyloxy;
in presence of the suitable base in a suitable solvent provides the compound of formula-4,

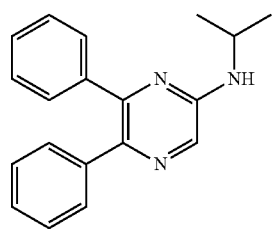

Formula-4 b) reacting the compound of formula-4 with the compound of general formula-5

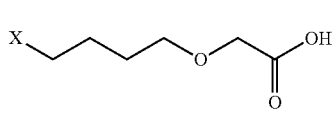

Formula-5

Wherein X is a leaving group such as halogen, mesyloxy or tosyloxy;
in presence of the suitable base in a suitable solvent provides provide formula-6,

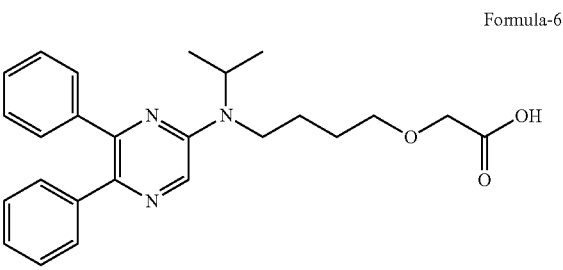 [SMILES: CC(C)N(CCCCOCC(=O)O)c1cnc(-c2ccccc2)c(-c2ccccc2)n1]

Formula-6 c) reacting the compound of formula-6 with methane sulfonamide in presence of a suitable coupling reagent in presence or absence of base in a suitable solvent provides the compound of formula-1,
d) optionally purifying the compound obtained in step-c) using a suitable solvent to get pure compound of formula-1.

Wherein, in step-a) to d) the suitable solvent is selected from hydrocarbon solvents, ketone solvents, ester solvents, alcohol solvents, chloro solvents, ether solvents, polar aprotic solvents, nitrile solvents, polar solvents and water or any mixture thereof;
in step-a) to c) the suitable base is selected from organic bases or inorganic bases and mixture thereof;
in step-c) the suitable coupling agent is selected form DCC, CDI, DIC, EDC.HCl, HATU and the like; optionally in combination with HOAt, HOBt, HOCt, TBTU, DMAP optionally in presence of a base.

Preferred embodiment of the present invention provides an improved process for the preparation of 2-{4-[(5,6-diphenylpyrazin-2-yl)(isopropyl)amino]butoxy}-N-(methylsulfonyl) acetamide compound of formula-1, comprising the following steps:
a) Reacting 2-amino-5,6-diphenylpyrazine compound of formula-2 with isopropyl bromide compound of formula-3a in presence of potassium tert-butoxide in dimethylformamide to provide N-isopropyl-5,6-diphenyl pyrazin-2-amine compound of formula-4,
b) reacting the compound of formula-4 with 2-(4-chlorobutoxy)acetic acid of formula-5a in presence of potassium carbonate in acetonitrile to provide 2-(4-((5,6-diphenylpyrazin-2-yl) (isopropyl) amino) butoxy)acetic acid compound of formula-6,
c) reacting the compound of formula-6 with methane sulfonamide in presence of HATU and triethylamine in dimethylformamide to provide the compound of formula-1.

The second aspect of the present invention provides an improved process for the preparation of 2-{4-[(5,6-diphenylpyrazin-2-yl)(isopropyl)amino]butoxy}-N-(methyl sulfonyl) acetamide compound of formula-1, comprising of:

a) Reacting the compound of formula-8

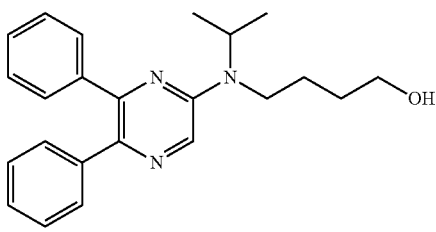
Formula-8 with the compound of general formula-9

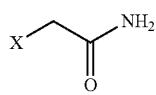
Formula-9 wherein X is a leaving group such as halogen, mesyloxy or tosyloxy;
in presence of the suitable base in the suitable solvent provides the compound of formula-10,

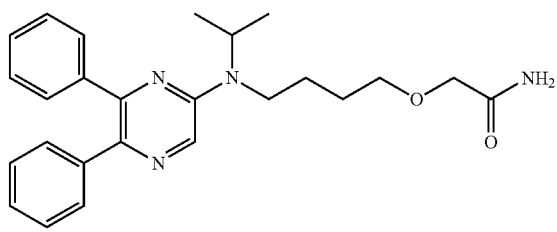
Formula-10 b) reacting the compound of formula-10 with methane sulfonyl chloride in a suitable solvent optionally in presence of a base provides the compound of formula-1,
c) optionally purifying the compound obtained in step-b) using a suitable solvent to get pure compound of formula-1.

Wherein, in step-a) to c) the suitable solvent is selected from hydrocarbon solvents, ketone solvents, ester solvents, alcohol solvents, chloro solvents, ether solvents, polar aprotic solvents and polar solvent like water or any mixture thereof;
in step-a) and b) the suitable base is selected from organic or inorganic base.

The third aspect of the present invention provides an improved process for the preparation of the compound of formula-4, comprising of:

a) Reacting the compound of general formula-7

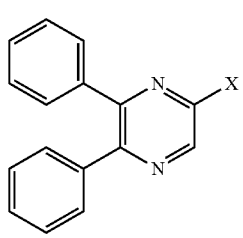
Formula-7

Wherein X is a leaving group such as halogen, mesyloxy or tosyloxy;
with isopropyl amine in presence or absence of a base in a suitable solvent provides the compound of formula-4,
b) optionally purifying the compound obtained in step-a) using a suitable solvent provides the pure compound of formula-4.

Wherein, in step-a) and b) the suitable solvent is selected from hydrocarbon solvents, ketone solvents, ester solvents, alcohol solvents, chloro solvents, ether solvents, polar aprotic solvents and polar solvent like water or their mixture thereof;
in step-a) a base is selected from organic or inorganic base.

Preferred embodiment of the present invention provides an improved process for the preparation of the compound of formula-4, comprising of: reacting 5-chloro-2,3-diphenylpyrazine of formula-7a with isopropyl amine to provide N-isopropyl-5,6-diphenylpyrazin-2-amine compound of formula-4.

The fourth aspect of the present invention provides an improved process for the preparation of the compound of formula-1, comprising of:

a) Reacting the compound of general formula-7 with isopropyl amine in presence or absence of a base in a suitable solvent provides the compound of formula-4,
b) optionally purifying the compound obtained in step-a) using a suitable solvent provides the pure compound of formula-4,
c) reacting the compound of formula-4 with the compound of general formula-5

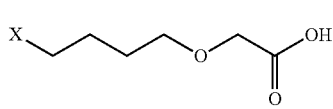
Formula-5

Wherein X is a leaving group such as halogen, mesyloxy or tosyloxy;
in presence of a suitable base in a suitable solvent provides the compound of formula-6,

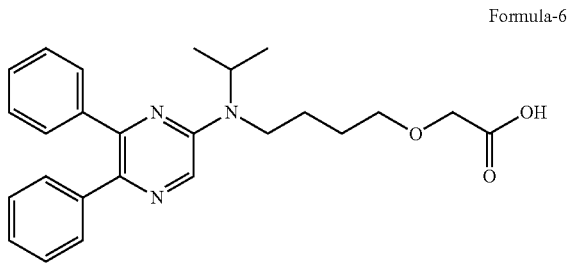 [SMILES: CC(C)N(CCCCOCC(=O)O)c1cnc(-c2ccccc2)c(-c2ccccc2)n1]
Formula-6 d) reacting the compound of formula-6 with methane sulfonamide in presence of a suitable coupling reagent in presence or absence of base in a suitable solvent provides the compound of formula-1,
e) optionally purifying the compound obtained in step-d) using a suitable solvent to get pure compound of formula-1.

Wherein, in steps-a) to e) the suitable solvent is selected from hydrocarbon solvents, ketone solvents, ester solvents, alcohol solvents, chloro solvents, ether solvents, polar aprotic solvents and polar solvent like water or their mixture thereof;

in step-a), c) and d) the suitable base is selected from organic or inorganic base;

in step-d) the suitable coupling agent is selected form DCC, CDI, DIC, EDC.HCl, HATU and the like; optionally in combination with HOAt, HOBt, HOCt, TBTU, DMAP optionally in presence of a base.

Preferred embodiment of the present invention provides an improved process for the preparation of compound of formula-1, comprising of:
a) Reacting the 5-chloro-2,3-diphenylpyrazine compound of formula-7a with isopropyl amine to provide the compound of N-isopropyl-5,6-diphenylpyrazin-2-amine compound of formula-4,
b) reacting the compound of formula-4 with 2-(4-chlorobutoxy)aceticacid of formula-5a in presence of potassium carbonate in acetonitrile to provide the 2-(4-((5,6-diphenyl pyrazin-2-yl)(isopropyl)amino)butoxy)acetic acid compound of formula-6,
c) reacting the compound of formula-6 with methane sulfonamide in presences of HATU and triethylamine in dimethylformamide to provide the compound of formula-1.

The fifth aspect of the present invention provides a novel process for the preparation of the compound of formula-6, comprising of:
a) Reacting the compound formula-8

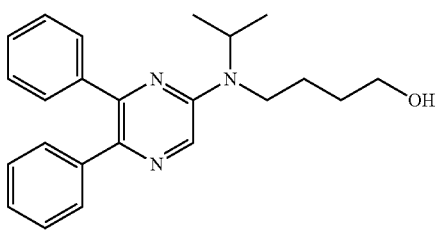

Formula-8 with the compound of general formula-11

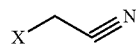

Formula-11 wherein X is a leaving group such as halogen, mesyloxy or tosyloxy;
in presence or absence of a base optionally in presence of a catalyst in a suitable solvent provides the compound of formula-12,

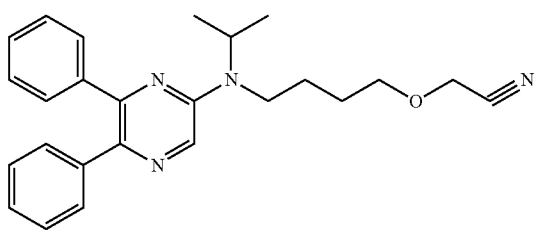

Formula-12 b) hydrolyzing the compound of formula-12 in presence of a suitable reagent in suitable solvent provides the compound of formula-6.

Wherein, in step-a) to b) the suitable solvent is selected from hydrocarbon solvents, ketone solvents, ester solvents, alcohol solvents, chloro solvents, ether solvents, polar aprotic solvents and polar solvents like water or their mixture thereof;

in step-a) the suitable base is selected from organic or inorganic base;

in step-b) the suitable reagent is acid or base.

Preferred embodiment of the present invention provides a novel process for the preparation of the compound of formula-6, comprising of:
a) Reacting the 4-((5,6-diphenylpyrazin-2-yl)(isopropyl)amino)butan-1-ol compound of formula-8 with chloro acetonitrile of formula-11a in presence of potassium carbonate and tetrabutyl ammonium bromide in acetone to provide 2-(4-((5,6-diphenylpyrazin-2-yl) (isopropyl) amino) butoxy) acetonitrile compound of formula-12,
b) treating the compound of formula-12 with sodium hydroxide in the mixture of methanol and water to provide the compound of 2-(4-((5,6-diphenylpyrazin-2-yl) (isopropyl)amino) butoxy)acetic acid of formula-6.

The sixth aspect of the present invention provides a novel process for the preparation of the compound of formula-1, comprising of:
a) Reacting the compound of formula-8 with the compound of general formula-11 in presence or absence of a base optionally in presence of a catalyst in a suitable solvent provides the compound of formula-12,
b) hydrolyzing the compound of formula-12 in presence of a suitable reagent in a suitable solvent provides the compound of formula-6,
c) reacting the compound of formula-6 with methane sulfonamide in presence of a suitable coupling reagent in presence or absence of base in a suitable solvent provides the compound of formula-1,
d) optionally purifying the compound obtained in step-c) to get pure compound of formula-1.

Wherein, in steps-a) to d) the suitable solvent is selected from hydrocarbon solvents, ketone solvents, ester solvents, alcohol solvents, chloro solvents, ether solvents, polar aprotic solvents and polar solvent like water or their mixture thereof;

in step-a) and c) the suitable base is selected from organic or inorganic base;

in step-b) the suitable reagent is acid or base.

in step-c) the suitable coupling agent is selected form DCC, CDI, DIC, EDC.HCl, HATU and the like; optionally in combination with HOAt, HOBt, HOCt, TBTU, DMAP optionally in presence of a base.

Preferred embodiment of the present invention provides an improved process for the preparation of the compound of formula-1, comprising of:
a) Reacting the 4-((5,6-diphenylpyrazin-2-yl)(isopropyl)amino)butan-1-ol compound of formula-8 with chloro acetonitrile compound of formula-11a in presence of potassium carbonate and tetrabutyl ammonium bromide in acetone to provide 2-(4-((5,6-diphenyl pyrazin-2-yl) (isopropyl) amino) butoxy) acetonitrile compound of formula-12,
b) treating the compound of formula-12 with sodium hydroxide in the mixture of methanol and water to provide 2-(4-((5,6-diphenylpyrazin-2-yl)(isopropyl)amino) butoxy)acetic acid compound of formula-6,
c) reacting the compound of formula-6 with methane sulfonamide in presences of HATU and triethylamine in dimethylformamide to provide the compound of formula-1.

The seventh aspect of the present invention provides a novel process for the preparation of the compound of formula-1, comprising of:
a) Reacting the compound of formula-8 with the compound of general formula-11 in presence or absence of a base optionally in presence of a catalyst in the suitable solvent provides the compound of formula-12,
b) hydrolyzing the compound of formula-12 in presence of a suitable reagent in a suitable solvent provides the compound of formula-10,
c) reacting the compound of formula-10 with methane sulfonyl chloride in the suitable solvent optionally in presence of a base provides the compound of formula-1,
d) optionally purifying the compound obtained in step-c) using the suitable solvent to get pure compound of formula-1.

Wherein, in step-a) to d) the suitable solvent is selected from hydrocarbon solvents, ketone solvents, ester solvents, alcohol solvents, chloro solvents, ether solvents, polar aprotic solvents and polar solvent like water or their mixture thereof;
in step-a) and c) the suitable base is selected from organic or inorganic base;
in step-b) the suitable reagent is acid or base.

The eighth aspect of the present invention provides a compound of formula-12.

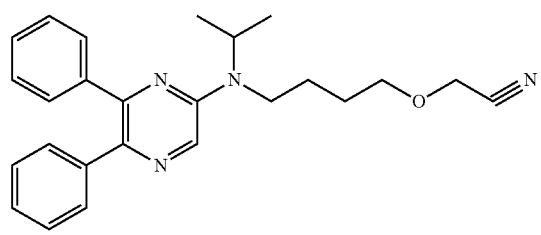

Formula-12

(2-(4-((5,6-diphenylpyrazin-2-yl) (isopropyl) amino) butoxy) acetonitrile) compound of formula-12 obtained according to the present invention is used for the preparation of the compound of formula-1.

The ninth aspect of the present invention provides an improved process for the preparation of the compound of general formula-5, comprising of reacting the compound of general formula-13 with the compound of general formula-14,

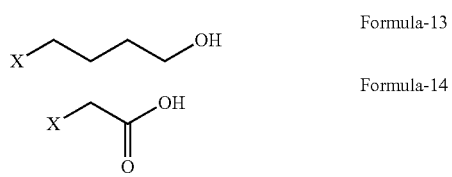

Wherein X is a leaving group such as halogen, mesyloxy or tosyloxy;
in presence or absence of a base in a suitable solvent provides the compound of general formula-5.

Preferred embodiment of the present invention provides an improved process for the preparation 2-(4-chlorobutoxy) aceticacid of formula-5a comprising of: reacting the compound of 1-chlorobutan-1-ol compound of formula-13a with 2-bromoaceticacid compound of formula-14a in presence of potassium carbonate in acetonitrile to provide 2-(4-chlorobutoxy)aceticacid of formula-5, which is the most use full intermediate in the preparation of compound of formula-1.

The Above Aspects of the Present Invention Can be Represented by Schematically as Follows:

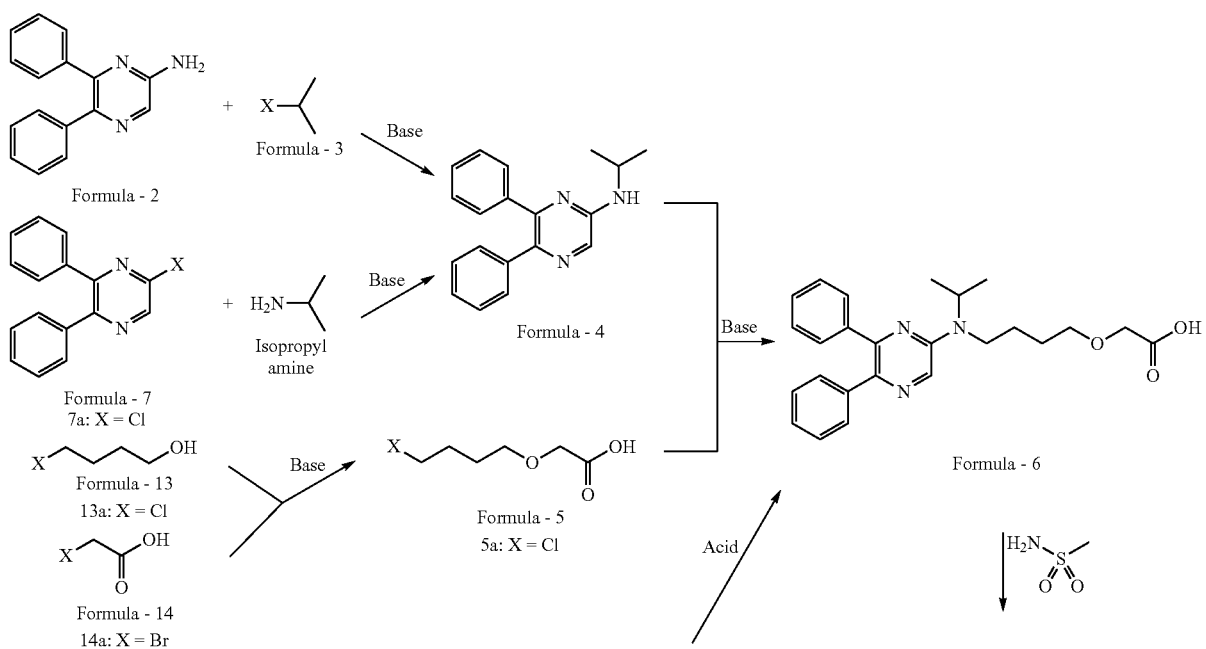

-continued

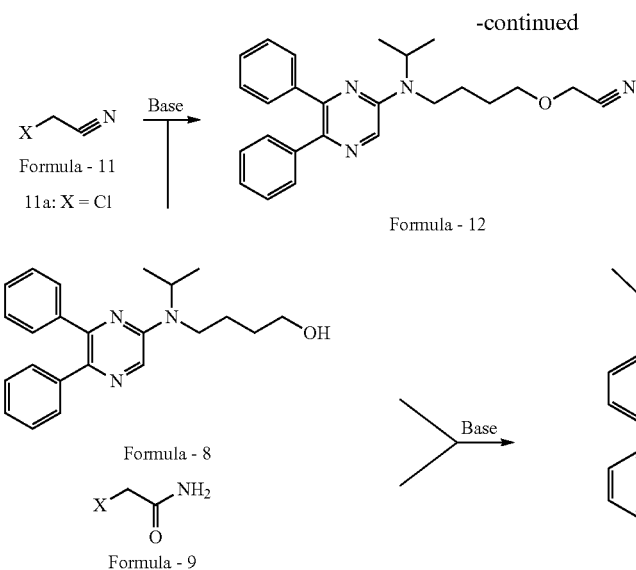

Formula - 11
11a: X = Cl

Formula - 12

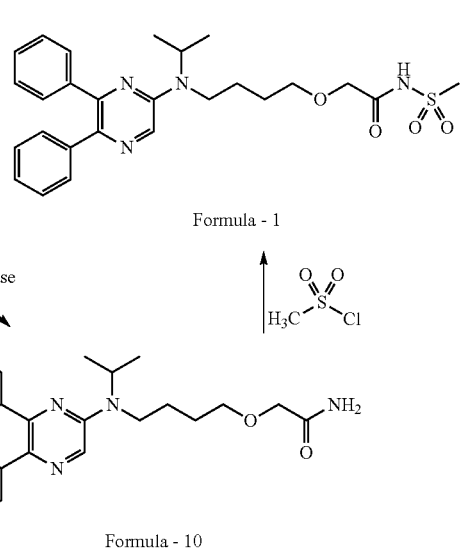

Formula - 1

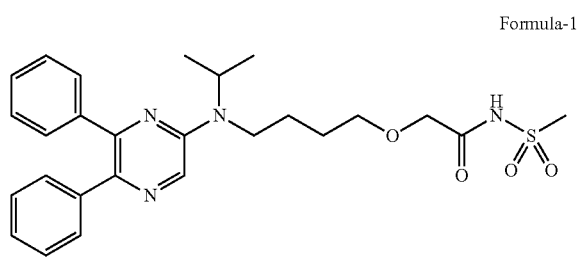 [SMILES: CC(C)N(CCCCOCC(=O)NS(C)(=O)=O)c1cnc(-c2ccccc2)c(-c2ccccc2)n1]

Formula - 8

Formula - 9

Wherein X is a leaving group such as halogen, mesyloxy or tosyloxy

Formula - 10

The tenth aspect of the present invention is an improved process for preparation of the compound of formula-1 comprising of:

Formula-1 a) Reacting the compound of general formula-7 with 4-(isopropylamino)-butan-1-ol compound of formula-15 in absence of solvent to provide compound of formula-8,
b) optionally purifying the compound obtained in step-a) by using a suitable solvent,
c) reacting the compound of formula-8 with 2-chloro-(N-methylsulfonyl) acetamide compound of formula-16 in presence of a suitable base in a suitable solvent to provide compound of formula-1,
d) optionally purifying the obtained compound in step-c) using suitable solvents.

Wherein, in step-b) to d) the suitable solvent is selected from hydrocarbon solvents, ketone solvents, ester solvents, alcohol solvents, chloro solvents, ether solvents, polar aprotic solvents and polar solvent like water or their mixture thereof;
in step-c) the suitable base is selected from organic or inorganic base;

The preferred embodiment of the present invention is an improved process for preparation of the compound of formula-1 comprising of:
a) Reacting 5-chloro-2,3-diphenylpyrazine compound of formula-7a with 4-(isopropylamino) butan-1-ol at 190-195° C. to provide 4-(5,6-diphenylpyrazin-2-yl)-isopropylamino butan-1-ol compound of formula-8,
b) purifying the compound obtained in step-a) using a mixture of acetone and n-heptane, c) reacting the compound obtained in step-b) with 2-chloro (N-methylsulfonyl)acetamide compound of formula-16 in presence sodium tert-butoxide in N-methylpyrrolidone to provide the compound of formula-1,
d) purifying the compound obtained in step-c) using a mixture ethyl acetate and ethanol.

An embodiment of the present invention provides a process for the purification of the compound of formula-8, comprising of:
a) Adding a solvent to the solution of 4-((5,6-diphenylpyrazin-2-yl)(isopropyl)amino) butan-1-ol compound of formula-8 in a suitable solvent at a suitable temperature,
b) stirring the reaction mixture at a suitable temperature,
c) filtering the solid obtained in step-b) to get pure compound of formula-8.

Wherein the suitable solvent is selected from hydrocarbon solvents, ketone solvents, ester solvents, alcohol solvents, chloro solvents, ether solvents, polar aprotic solvents and polar solvent like water or their mixture thereof.

Preferred embodiment of the present invention provides a process for the purification of the compound of formula-8, comprising of:
a) Adding n-heptane to the solution of 4-((5,6-diphenylpyrazin-2-yl)(isopropyl)amino) butan-1-ol compound of formula-8 in acetone at 0-10° C.,
b) stirring the reaction mixture at 0-10° C.,
c) filtering the solid obtained in step-b) to get pure compound of formula-8.

The Above Aspect of the Present Invention Can be Represented by Schematically as Follows:

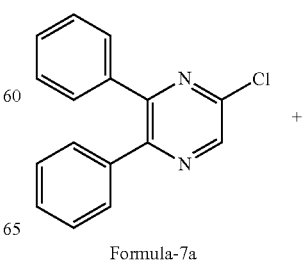

Formula-7a

+

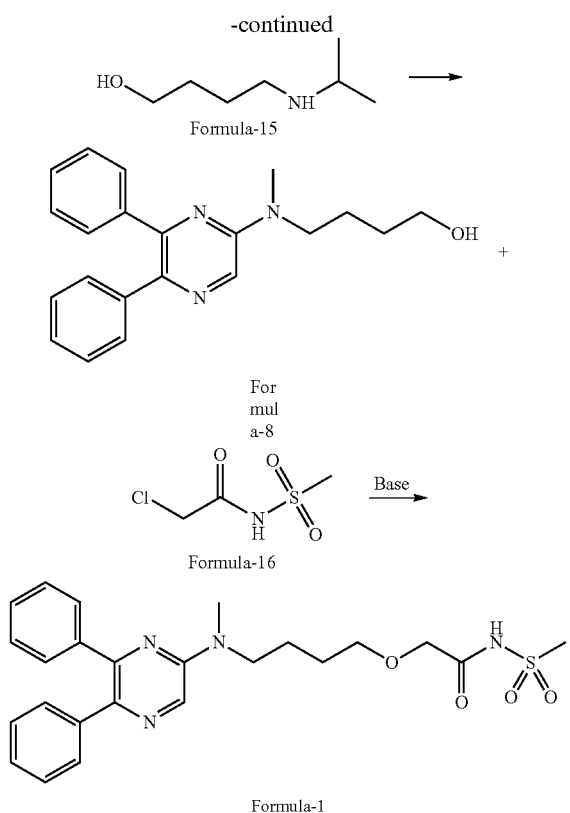

Formula-15

Formula-8

Formula-16

Formula-1

The eleventh aspect of the present invention provides crystalline form-P of 2-{4-[(5,6-diphenylpyrazin-2-yl)(isopropyl)amino]butoxy}-N-(methylsulfonyl) acetamide compound of formula-1. The crystalline form-P of the present invention is characterized by its powder X-Ray diffraction pattern having peaks at about 3.3, 6.6, 9.7, 12.6, 13.3, 13.5, 16.2, 17.4, 18.1, 18.6, 19.1, 19.3, 19.7, 20.3, 21.3, 23.0 & 27.9±0.2° 2θ. The said crystalline form-P is further characterized by its powder X-Ray diffraction pattern substantially in accordance with FIG. 7, by its IR spectrum shown in FIG. 8 and its DSC thermogram shown in FIG. 9.

The twelfth aspect of the present invention provides a process for the preparation of the crystalline form-P of 2-{4-[(5,6-diphenylpyrazin-2-yl)(isopropyl)amino]butoxy}-N-(methyl sulfonyl) acetamide compound of formula-1; comprising of:
a) Melting or heating the compound of formula-1 at a suitable temperature optionally under reduced pressure,
b) combining the obtained compound in step-a) to the solvent system,
c) stirring the reaction mixture at a suitable temperature,
d) filtering the obtained solid in step-c) provides the crystalline form-P of 2-{4-[(5,6-diphenylpyrazin-2-yl)(isopropyl) amino]butoxy}-N-(methylsulfonyl) acetamide compound of formula-1.
Wherein in step-a) the suitable temperature is 100 to 150° C., preferably 130-145° C.;
in step b) the solvent system may be a single solvent or mixture of solvents and is selected from hydrocarbon solvents, ester solvents, chloro solvents, ketone solvents; preferably hydrocarbon solvents; most preferably n-heptane;
in step c) the suitable temperature is below 40° C., further stirring the reaction mixture for more than 24 hours.

The term "melting" refers to "heating the compound up to completely melted the compound" at a suitable temperature optionally under reduced pressure.

Preferred embodiment of the present invention provides a process for the preparation of the crystalline form-P of 2-{4-[(5,6-diphenylpyrazin-2-yl)(isopropyl)amino]butoxy}-N-(methyl sulfonyl) acetamide compound of formula-1; comprising of:
a) Melting the compound of formula-1 at 135-145° C. under reduced pressure,
b) adding the obtained compound in step-a) to pre-cooled n-heptane,
c) stirring the reaction mixture at below 30° C.,
d) filtering the obtained solid in step-c) provides the crystalline form-P of 2-{4-[(5,6-diphenylpyrazin-2-yl)(isopropyl) amino]butoxy}-N-(methylsulfonyl) acetamide compound of formula-1.

Another embodiment of the present invention provides a process for the preparation of the crystalline form-P of 2-{4-[(5,6-diphenylpyrazin-2-yl)(isopropyl)amino]butoxy}-N-(methyl sulfonyl) acetamide compound of formula-1; comprising of:
a) Melting the compound of formula-1 at 135-145° C. under reduced pressure,
b) adding the obtained compound in step-a) to n-heptane,
c) stirring the reaction mixture at 30-40° C.,
d) filtering the obtained solid in step-c) provides the crystalline form-P of 2-{4-[(5,6-diphenylpyrazin-2-yl)(isopropyl) amino]butoxy}-N-(methylsulfonyl) acetamide compound of formula-1.

Another embodiment of the present invention provides a process for the preparation of the crystalline form-P of 2-{4-[(5,6-diphenylpyrazin-2-yl)(isopropyl)amino]butoxy}-N-(methyl sulfonyl) acetamide compound of formula-1; comprising of:
a) Heating the compound of formula-1 at 150-170° C.,
b) adding the obtained compound in step-a) to n-heptane,
c) stirring the reaction mixture for 30 to 50 hours at below 35° C.,
d) filtering the obtained solid in step-c) provides the crystalline form-P of 2-{4-[(5,6-diphenylpyrazin-2-yl)(isopropyl) amino]butoxy}-N-(methylsulfonyl) acetamide compound of formula-1.

Further embodiment of the present invention provides another process for the preparation of the crystalline form-P of 2-{4-[(5,6-diphenylpyrazin-2-yl)(isopropyl)amino]butoxy}-N-(methyl sulfonyl) acetamide compound of formula-1; comprising of:
a) Suspending amorphous form of 2-{4-[(5,6-diphenylpyrazin-2-yl)(isopropyl)amino] butoxy}-N-(methyl sulfonyl) acetamide compound of formula-1 in a suitable solvent,
b) stirring the suspension for 36 to 40 hours at a suitable temperature,
c) filtering the solid provides the crystalline form-P of 2-{4-[(5,6-diphenylpyrazin-2-yl)(isopropyl) amino]butoxy}-N-(methylsulfonyl) acetamide compound of formula-1.

The thirteenth aspect of the present invention provides crystalline form-L of 2-{4-[(5,6-diphenylpyrazin-2-yl)(isopropyl)amino]butoxy}-N-(methylsulfonyl) acetamide compound of formula-1. The crystalline form-L of the present invention is characterized by its powder X-Ray diffraction pattern having peaks at about 3.3, 4.2, 6.6, 11.8, 12.6, 13.5, 16.2, 17.4, 18.1, 18.6, 19.1, 19.3, 19.7, 20.3, 21.3, 23.0 & 27.9±0.2° 2θ. The said crystalline form-L is further characterized by its powder X-Ray diffraction pattern substantially in accordance with FIG. 10 and its DSC thermogram shown in FIG. 11.

The fourteenth aspect of the present invention provides a process for the preparation of crystalline form-L of 2-{4-[(5,6-diphenylpyrazin-2-yl)(isopropyl)amino]butoxy}-N-(methyl sulfonyl) acetamide compound of formula-1; comprising of:
a) Heating the compound of formula-1 a suitable temperature,
b) combining the obtained compound in step-a) to a solvent system,
c) stirring the reaction mixture at a suitable temperature,
d) filtering the obtained solid in step-c) provides the crystalline form-L of 2-{4-[(5,6-diphenyl pyrazin-2-yl)(isopropyl) amino]butoxy}-N-(methylsulfonyl) acetamide compound of formula-1.

Wherein in step-a) the suitable temperature is 100 to 180° C., preferably 130-170° C.;
in step b) the solvent system may be a single solvent or mixture of solvents and is selected from hydrocarbon solvents, ester solvents, chloro solvents, ketone solvents; preferably hydrocarbon solvents; most preferably n-heptane; in step c) the suitable temperature is below 40° C., further stirring the reaction mixture for 2 to 20 hours.

Preferred embodiment of the present invention provides a process for the preparation of the crystalline form-L of 2-{4-[(5,6-diphenylpyrazin-2-yl)(isopropyl)amino]butoxy}-N-(methyl sulfonyl) acetamide compound of formula-1; comprising of:
a) Heating the compound of formula-1 to 130-170° C.,
b) adding the compound obtained in step-a) to n-heptane,
c) stirring the reaction mixture for 2 to 20 hours at below 35° C.,
d) filtering the obtained solid in step-c) provides the crystalline form-L of 2-{4-[(5,6-diphenylpyrazin-2-yl)(isopropyl) amino]butoxy}-N-(methylsulfonyl) acetamide compound of formula-1.

The fifteenth aspect of the present invention provides a crystalline form-M of the compound of formula-1. The crystalline form-M of the present invention is characterized by its powder X-Ray diffraction pattern having peaks at about 3.3, 13.6, 18.1, 20.3 & 21.4±0.2 degrees of 2-theta and further it is depicted in FIG. 1.

The sixteenth aspect of the present invention is to provide a process for the preparation of form-M of 2-{4-[(5,6-diphenylpyrazin-2-yl)(isopropyl)amino]butoxy}-N-(methylsulfonyl) acetamide compound of formula-1 comprising of:
a) Heating the mixture of the compound of formula-1 and a suitable of solvents at a suitable temperature,
b) optionally filtered the reaction mixture,
c) distilling off the solvent from the filtrate,
d) adding a suitable solvent to the residue obtained in step-c,
e) filtering the obtained solid in step-d) provides the crystalline form-M of 2-{4-[(5,6-diphenyl pyrazin-2-yl)(isopropyl) amino]butoxy}-N-(methylsulfonyl) acetamide compound of formula-1.

Preferred embodiment of the present invention provides a process for the preparation of the crystalline form-M of 2-{4-[(5,6-diphenylpyrazin-2-yl)(isopropyl)amino]butoxy}-N-(methyl sulfonyl) acetamide compound of formula-1; comprising of:
a) Heating the mixture of the compound of formula-1 and a mixture of ethyl acetate and water to reflux temperature,
b) filtering the reaction mixture,
c) distilling off the solvent from the filtrate,
d) adding n-heptane to the obtained residue in step-c),
e) filtering the obtained solid in step-d) provides the crystalline form-M of 2-{4-[(5,6-diphenyl pyrazin-2-yl)(isopropyl) amino]butoxy}-N-(methylsulfonyl) acetamide compound of formula-1.

The seventeenth aspect of the present invention provides a process for the preparation of the crystalline form-D of 2-{4-[(5,6-diphenylpyrazin-2-yl)(isopropyl)amino]butoxy}-N-(methyl sulfonyl) acetamide compound of formula-1; comprising of:
a) Melting the compound of formula-1 at a suitable temperature optionally under reduced pressure,
b) adding the obtained compound in step-a) to pre-cooled solvent system,
c) stirring the reaction mixture at a suitable temperature,
d) filtering the obtained solid in step-c) provides the crystalline form-D of 2-{4-[(5,6-diphenylpyrazin-2-yl)(isopropyl) amino]butoxy}-N-(methylsulfonyl) acetamide compound of formula-1.

Wherein in step-a) the suitable temperature is 90 to 150° C., preferably 140-150° C.;
in step b) the solvent system may be a single solvent or mixture of solvents and is selected from hydrocarbon solvents, ester solvents, chloro solvents, ketone solvents; preferably hydrocarbon solvents; most preferably n-heptane;
in step c) the suitable temperature is below 30° C.

Preferred embodiment of the present invention provides a process for the preparation of the crystalline form-D of 2-{4-[(5,6-diphenylpyrazin-2-yl)(isopropyl)amino]butoxy}-N-(methyl sulfonyl) acetamide compound of formula-1; comprising of:
a) Melting the compound of formula-1 at 140-150° C. under reduced pressure,
b) adding the obtained compound in step-a) to pre-cooled n-heptane,
c) stirring the reaction mixture for 1 hour at 0-5° C.,
d) filtering the obtained solid in step-c) provides the crystalline form-D of 2-{4-[(5,6-diphenyl pyrazin-2-yl) (isopropyl) amino]butoxy}-N-(methylsulfonyl) acetamide compound of formula-1.

Figure 2:
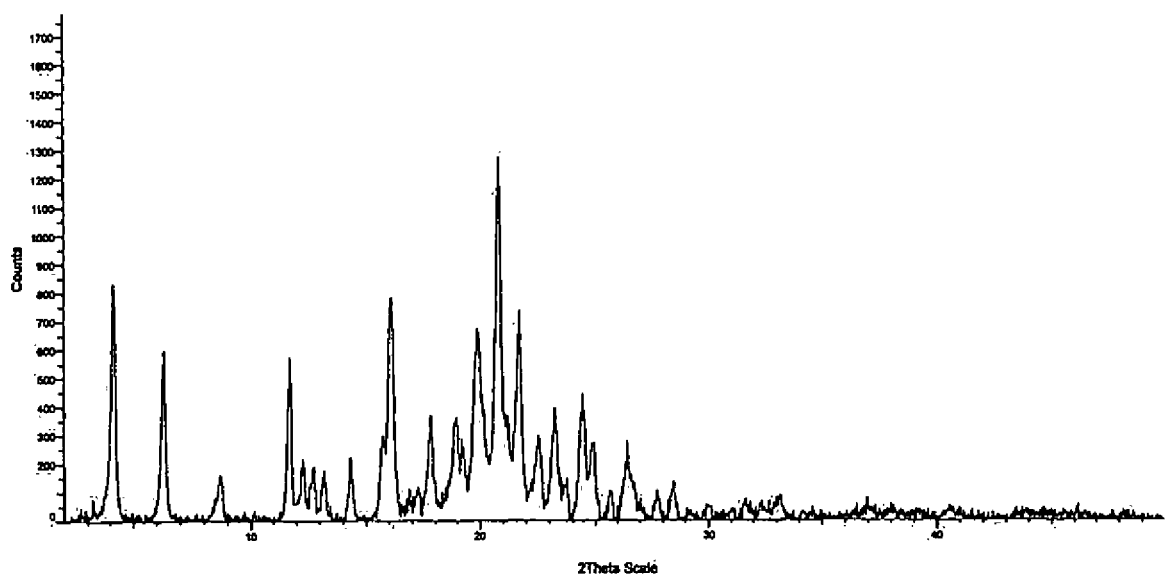
FIG. 2: Illustrates the PXRD pattern of crystalline form-D of 2-{4-[(5,6-diphenylpyrazin-2-yl) (isopropyl) amino]butoxy}-N-(methylsulfonyl) acetamide compound of formula-1.
Figure 3:
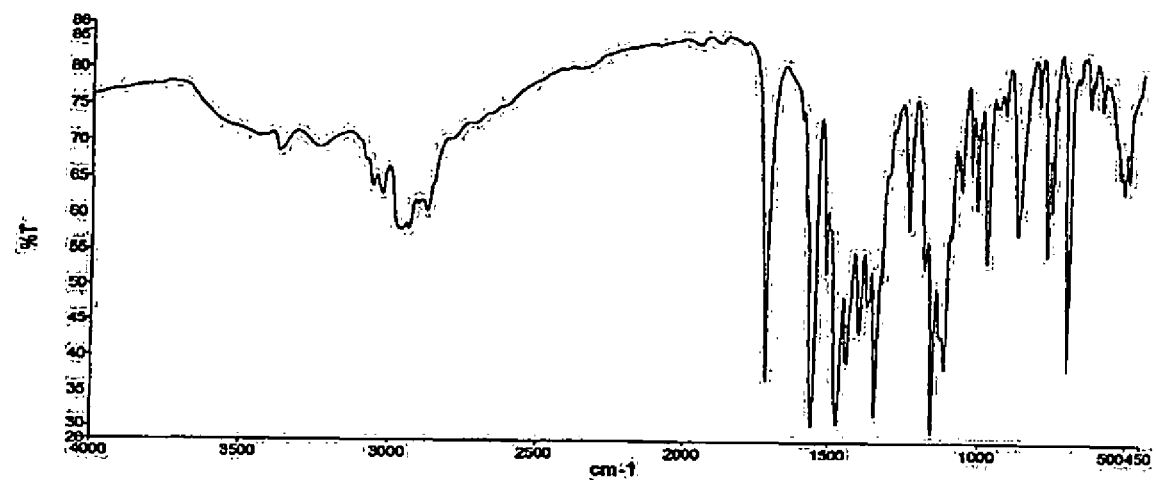
FIG. 3: Illustrates the IR spectrum of crystalline form-D of 2-{4-[(5,6-diphenylpyrazin-2-yl)(isopropyl) amino]butoxy}-N-(methylsulfonyl) acetamide compound of formula-1.
Figure 4:
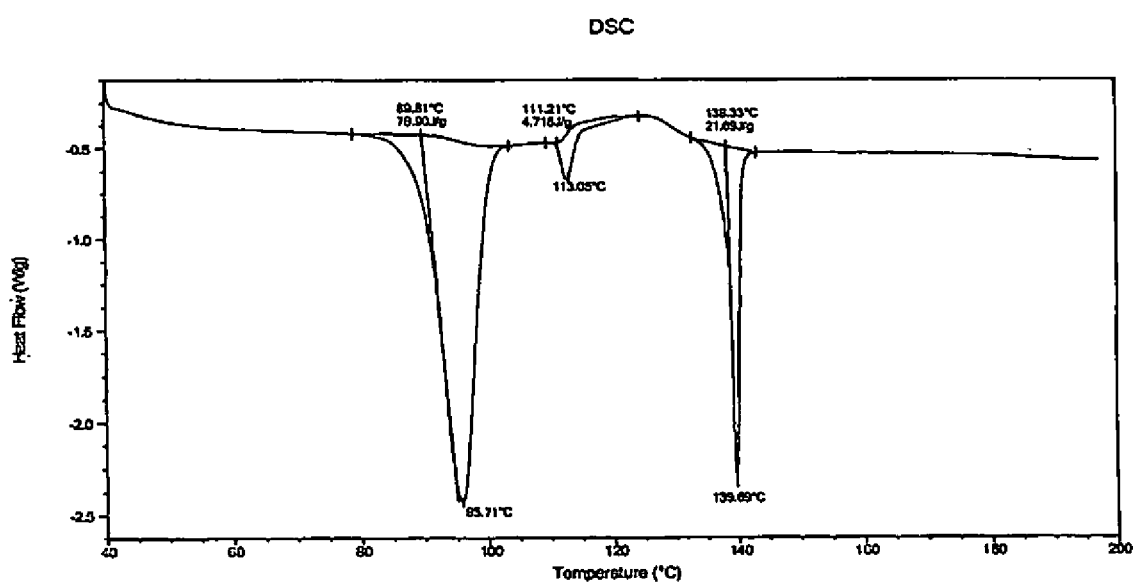
FIG. 4: Illustrates the DSC thermogram of crystalline form-D of 2-{4-[(5,6-diphenylpyrazin-2-yl) (isopropyl) amino]butoxy}-N-(methylsulfonyl) acetamide compound of formula-1.

Further aspect of the present invention is to provide the crystalline form-D of 2-{4-[(5,6-diphenylpyrazin-2-yl)(isopropyl)amino]butoxy}-N-(methyl sulfonyl) acetamide compound of formula-1 characterized by its PXRD pattern having peaks at about 4.1, 6.3, 11.7, 12.2, 16.0, 17.8, 19.9, 20.8, 21.7, 23.2 & 24.4±0.2° 2θ and its PXRD pattern as illustrated in FIG. 2, its DSC in illustrated in FIG. 4 and its IR spectrum is illustrated in FIG. 3.

The eighteenth aspect of the present invention provides a process for the preparation of an amorphous form of 2-{4-[(5,6-diphenylpyrazin-2-yl)(isopropyl)amino] butoxy}-N-(methyl sulfonyl)acetamide compound of formula-1.

Figure 5:
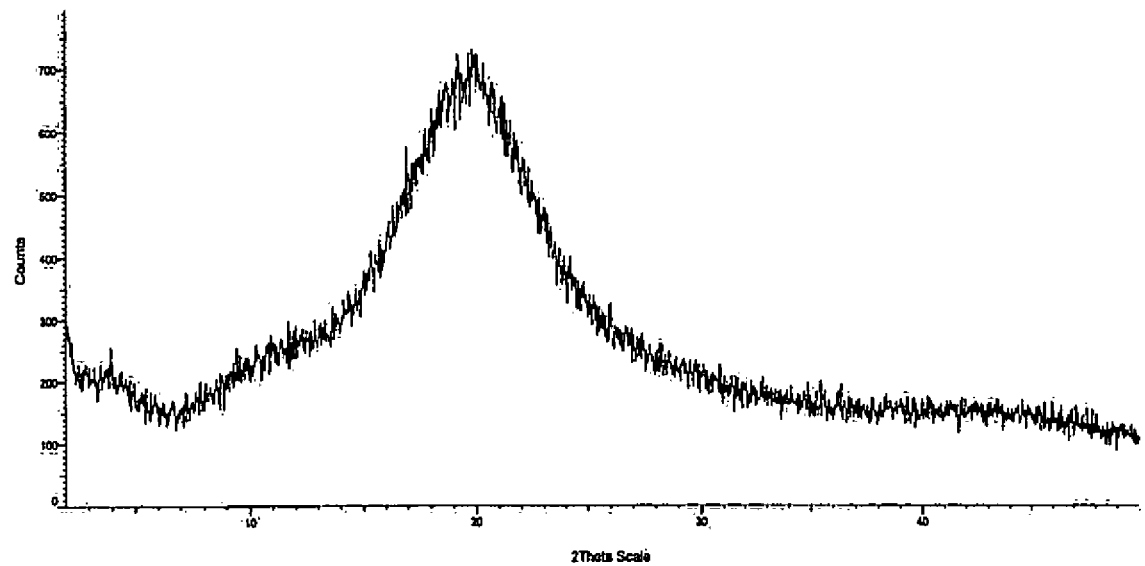
FIG. 5: Illustrates the PXRD pattern of an amorphous form of 2-{4-[(5,6-diphenylpyrazin-2-yl) (isopropyl) amino]butoxy}-N-(methylsulfonyl) acetamide compound of formula-1.

Preferred embodiment of the present invention provides a process for the preparation of amorphous of 2-{4-[(5,6-diphenylpyrazin-2-yl)(isopropyl)amino]butoxy}-N-(methyl sulfonyl) acetamide compound of formula-1; comprising of:
a) Heating the compound of formula-1 at 140-170° C. under reduced pressure,
b) cooling the obtained residue to below 25° C.,
c) drying the obtained solid to provide an amorphous form of 2-{4-[(5,6-diphenyl pyrazin-2-yl) (isopropyl) amino] butoxy}-N-(methylsulfonyl) acetamide compound of formula-1 and its PXRD pattern is shown in FIG. 5.

2-{4-[(5,6-diphenylpyrazin-2-yl)(isopropyl)amino]butoxy}-N-(methylsulfonyl) acetamide and its polymorphs produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

PXRD analysis of 2-{4-[(5,6-diphenylpyrazin-2-yl)(isopropyl)amino]butoxy}-N-(methylsulfonyl) acetamide was carried out using BRUKER D8 ADVANCED/AXS X-Ray diffractometer using Cu Kα radiation of wavelength 1.5406 A° and continuous scan speed of 0.03°/min. IR spectra were recorded on a Perkin-Elmer FTIR spectrometer.

Differential scanning calorimetric (DSC) analysis was performed on Q10 V9.9 Build 303 calorimeter (or) Q2000 V24.11 Build 124 calorimeter with aluminium pans, heating the samples from 40 to 200° C. under closed conditions at a rate of 10.00° C./min.

IR spectra were recorded on a Perkin-Elmer FTIR spectrometer.

HPLC Analysis Method of 2-{4-[(5,6-diphenylpyrazin-2-yl)(isopropyl)amino]butoxy}-N-(methylsulfonyl)acetamide Apparatus: A liquid chromatographic system, equipped with variable wavelength UV-Detector. Column: Kromasil C18, 250*4.6, 5μ or equivalent; Wavelength: 210 nm, Column temperature: 30° C.; Injection volume: 10 μL; Elution: Gradient; Buffer: Transfer 1.0 mL of Orthophosphoric acid (85%) into 1000 mL of Milli-Q-Water, mix well. Filter this solution through 0.22 μm nylon membrane filter paper.

Mobile Phase-A: Buffer (100%), Mobile Phase-B: Acetonitrile:Water (90:10 v/v).

The following impurities are identified during the process for the preparation of the compound of formula-1:

1. Acid impurity {2-{4-[N-(5,6-diphenylpyrazin-2-yl)-N-isopropylamino] butyloxy}acetic acid}:

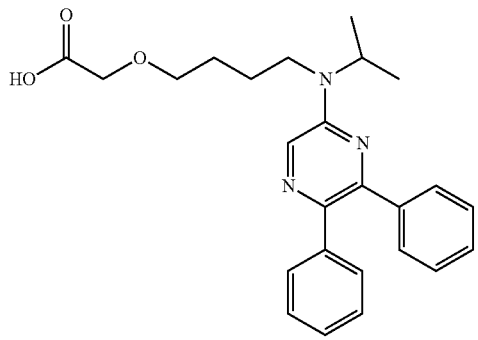 [SMILES: CC(C)N(CCCCOCC(=O)O)c1cnc(-c2ccccc2)c(-c2ccccc2)n1]

2. Tertiary butylester impurity {tert-butyl 2-(4-((5,6-diphenylpyrazin-2-yl) (isopropyl) amino) butoxy)acetate}

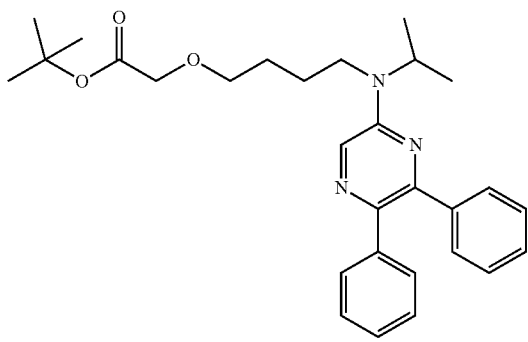 [SMILES: CC(C)N(CCCCOCC(=O)OC(C)(C)C)c1cnc(-c2ccccc2)c(-c2ccccc2)n1]

3. Ethyl ester impurity {Ethyl 2-(4-((5,6-diphenylpyrazin-2-yl)(isopropyl) amino) butoxy)acetate}

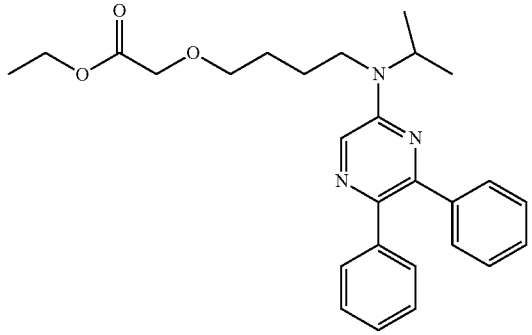 [SMILES: CCOC(=O)COCCCCN(c1cnc(-c2ccccc2)c(-c2ccccc2)n1)C(C)C]

The process described in the present invention was demonstrated in examples illustrated below. These examples are provided as illustration only and therefore should not be construed as limitation of the scope of the invention.

EXAMPLES

Example-1 Preparation of 4-((5,6-diphenylpyrazin-2-yl)(isopropyl)amino)butan-1-ol Compound of Formula-8

A mixture of 5-chloro-2,3-diphenylpyrazine (25 gm) compound of formula-7a and 4-(isopropyl amino)butan-1-ol (108 gm) was heated to 190-195° C. and stirred the reaction mixture for 10-12 hours at same temperature. Cooled the reaction mixture to 25-35° C. To this reaction mixture n-heptane followed by water were added slowly at 25-30° C. and stirred the reaction mixture for 2 hours at the same temperature. Filter the precipitated solid, washed with water and dried to get the title compound.

Yield: 30 gm.

Example-2: Preparation of tert-butyl 2-(4-((5,6-diphenylpyrazin-2-yl)(isopropyl)amino)butoxy)acetate Potassium hydroxide solution (96.6 gm of potassium hydroxide dissolved in 175 ml of water) was added to the mixture of 4-((5,6-diphenylpyrazin-2-yl)(isopropyl)amino) butan-1-ol (25 gm) and toluene (175 ml) at 25-30° C. and stirred the reaction mixture for 30 minutes at the same temperature. Cooled the reaction mixture to 0-5° C. Tert-butyl bromoacetate (94 gm) was slowly added to the reaction mixture at 0-5° C. and stirred the reaction for 60 minutes at same temperature. Raised the temperature of the reaction mixture to 25-30° C. and maintained for 60 minutes. Both the aqueous and organic layers were separated. The aqueous layer was extracted with toluene and combined the organic layers. Organic layer was washed with hydrochloric acid solution followed by with aqueous sodium bicarbonate solution. Organic layer was dried with sodium sulphate and distilled off the solvent completely from the organic layer under reduced pressure to get the title compound.

Yield: 29 gm.

Example-3: Preparation of 2-(4-((5,6-diphenylpyrazin-2-yl)(isopropyl)amino)butoxy)acetic acid Compound of Formula-6

Aqueous sodium hydroxide solution (7.5 gm of sodium hydroxide was dissolved in 80 ml of water) was added to the solution of tert-butyl 2-(4-((5,6-diphenylpyrazin-2-yl)(isopropyl) amino)butoxy)acetate (30 gm) in methanol (290 ml) at 30-35° C. Heated the reaction mixture to reflux temperature and stirred for 3 hours at the same temperature. Distilled off solvent completely from the reaction mixture under reduced pressure and cooled the reaction mixture to 25-30° C. Water was added to the obtained compound and acidified the reaction mixture using diluted hydrochloric acid at the same temperature. Extracted the reaction mixture with ethyl acetate. The organic layer was washed with aqueous sodium chloride solution and dried with sodium sulphate. Distilled off the solvent from the organic layer under reduced pressure. Diisopropyl ether (60 ml) was added to the obtained compound at 25-30° C. and stirred for 60 minutes at the same temperature. Filtered the precipitated solid, washed with diisopropyl ether and dried to get the title compound.

Yield: 19 gm.

Example-4: Preparation of 2-{4-[(5,6-diphenylpyrazin-2-yl)(isopropyl)amino]butoxy}-N-(methylsulfonyl)acetamide Compound of Formula-1

Triethylamine (9.6 gm) was added to the mixture of 2-(4-((5,6-diphenylpyrazin-2-yl)(isopropyl)amino)butoxy) acetic acid (10 gm), dichloromethane (100 ml), N,N-dicyclohexylcarbodiimide (4.9 gm), hydroxybenzotriazole (3.5 gm) and methane sulfonamide (3.39 gm) at 25-30° C. and stirred the reaction mixture for 12 hours at the same temperature. Filtered the unwanted compounds from the reaction mixture and washed with dichloromethane. The organic layer was washed with water, followed by with aqueous citric acid solution and then washed with aqueous sodium chloride solution. Distilled off the solvent from the organic layer under reduced pressure. To this residue ethyl acetate (20 ml) and carbon (1 gm) were added at 25-30° C. and stirred the reaction mixture for 30 minutes at the same temperature. Filtered the reaction mixture through hyflow bed and washed with ethyl acetate. The obtained filtrate was slowly added to the mixture of n-heptane and water at 25-30° C. and stirred for 10 hours. Filtered the precipitated solid, washed with n-heptane and dried to get the title compound.

Yield: 4.5 gm.

Example-5: Preparation of 2-{4-[(5,6-diphenylpyrazin-2-yl)(isopropyl)amino]butoxy}-N-(methylsulfonyl)acetamide Compound of Formula-1

Sodium t-butoxide (96.6 gm) was added to the mixture of n-methy pyrrolidinone (125 ml) and 4-((5,6-diphenylpyrazin-2-yl)(isopropyl)amino)butan-1-ol (25 gm) compound of formula-8 at 0-5° C. and stirred the reaction for 20 minutes at the same temperature. 2-chloro-N-(methylsulfonyl)acetamide (23.7 gm) was slowly added to the reaction mixture at 0-5° C. and raise the temperature of the reaction mixture to 25-30° C. Stirred the reaction mixture for 10-12 hours at 25-30° C. and water was added to it at the same temperature. The reaction mixture was extracted with ethyl acetate. The organic layer was washed with aqueous sodium chloride solution and distilled off the solvent from the organic layer under reduced pressure. To this residue ethyl acetate (50 ml) and carbon (2.5 gm) were added at 25-30° C. and stirred the reaction mixture for 30 minutes at the same temperature. Filtered the reaction mixture through hyflow bed and washed with ethyl acetate. The obtained filtrate was slowly added to the mixture of n-heptane and water at 25-30° C. and stirred for 10 hours. Filtered the precipitated solid, washed with n-heptane and dried to get the title compound.

Yield: 14 gm.

Example-6: Preparation of 2-chloro-N-(methylsulfonyl)acetamide

A mixture of methane sulfonamide (100 gm) and chloroacetyl chloride (356.4 gm) was heated to reflux temperature and stirred it for 10 hours at the same temperature. Cooled the reaction mixture to −10 to −5° C. and stirred it for 2 hours at the same temperature. Filtered the precipitated, solid, washed with toluene followed by n-heptane and dried to get the title compound.

Yield: 175 gm.

Example-7: Purification of the Compound of Formula-1

Methanol (20 ml) was added to the compound of formula-1 (2 gm) at 25-30° C. and heated to reflux temperature. Dichloromethane (3 ml) was added to the reaction mixture at reflux temperature and stirred for 15 minutes at the same temperature. Filtered the reaction mixture, distilled off the solvent from the filtrate under reduced pressure to get the title compound.

Yield: 2 gm

Example-8: Preparation of N-isopropyl-5,6-diphenylpyrazin-2-amine (Formula-4)

Isopropyl bromide (5.5 gm) was added to the mixture of 2-amino-5,6-diphenylpyrazine (10 gm), potassium tert-butoxide (9 gm) and dimethylformamide (50 ml) at 25-30° C., slowly heated to 80-85° C. and stirred the reaction mixture for 6 hours at same temperature. The reaction mixture was cooled to 10-15° C., diluted the reaction mixture with water and stirred it for 2 hours at the same temperature. Filtered the obtained solid and dried to get the title compound.

Yield: 9.5 gm

Example-9: Preparation of N-isopropyl-5,6-diphenylpyrazin-2-amine (Formula-4)

A mixture of 5-chloro-2,3-diphenylpyrazine (10 gm), isopropyl amine (7.5 gm) and potassium carbonate (10.5 gm) and dioxane (50 ml) were heated to 40-45° C. and stirred the reaction mixture for 12 hrs at the same temperature. The reaction mixture was cooled to 10-15° C., diluted with water and extracted with dichloromethane. Combined the organic layers was washed with aqueous sodium hydrochloride solution and dried over anhydrous sodium sulphate. Distilled off the solvent completely from the organic layer under reduced pressure to provide the title compound.

Yield: 9 gm

Example-10: Preparation of 2-(4-chlorobutoxy)aceticacid (Formula-5a)

2-bromoaceticacid (10 gm) was slowly added to a mixture of 1-chlorobutan-4-ol (7.2 gm), potassium carbonate (26.5 gm) and acetonitrile (50 ml) at 25-30° C. The reaction mixture was heated to 75-80° C. and stirred the reaction mixture for 6 hours at same temperature. The reaction mixture was cooled to 25-30° C. and diluted with water. Acidified the reaction mixture using diluted hydrochloric acid at 25-30° C. The reaction mixture extracted with dichloromethane. Combined the organic layers was dried over anhydrous sodium sulphate and distilled off the solvent under reduced pressure to provide the title compound.

Yield: 10.5 gm.

Example-11: Preparation of 2-(4-((5,6-diphenylpyrazin-2-yl)(isopropyl)amino)butoxy)acetic acid (Formula-6)

A mixture of N-isopropyl-5,6-diphenylpyrazin-2-amine (8 gm), potassium carbonate (7.5 gm) and acetonitrile (40 ml) was stirred for 1 hr at 25-30° C. A solution of 2-(4-chlorobutoxy) aceticacid (5.4 gm) in acetonitrile (15 ml) was slowly added to the reaction mixture at 25-30° C. Heated the reaction mixture to reflux and stirred for 12 hours at the same temperature. The reaction mixture was cooled to 10-15° C. and diluted with water. Acidified the reaction mixture using diluted hydrochloric acid and extracted the reaction mixture using ethyl acetate. Combined the organic layers and dried over sodium sulphate. Distilled off the solvent completely from the organic layer to get the title compound.

Yield: 8.5 gm

Example-12: Preparation of 2-(4-((5,6-diphenylpyrazin-2-yl)(isopropyl)amino)butoxy)-N-(methylsulfonyl)acetamide (Formula-1)

A mixture of 2-(4-((5,6-diphenylpyrazin-2-yl)(isopropyl)amino)butoxy)acetic acid (5 gm), HATU (5.4 gm), triethylamine (1.5 gm) and dimethylformamide (20 ml) was stirred for 1 hr at 5-10° C. under nitrogen atmosphere. Methane sulfonamide (5.2 gm) was slowly added to the reaction mixture at 5-10° C. and stirred for 12 hrs at the same temperature. The reaction mixture was diluted with water and stirred for 2 hrs. The precipitated solid was filtered and dried to get the title compound.

Yield: 4.5 gm

Example-13: Preparation of 2-(4-((5,6-diphenylpyrazin-2-yl)(isopropyl)amino)butoxy)acetonitrile (Formula-12)

To the mixture of 4-((5,6-diphenylpyrazin-2-yl)(isopropyl)amino)butan-1-ol (10 gm), tetrabutyl ammoniumbromide (0.2 gm), potassium carbonate (7.6 gm) and acetone (50 mL), chloroacetonitrile (3.2 gm) was added at 25-30° C. Heated the reaction mixture to reflux temperature and stirred the reaction mixture for 6 hrs at the same temperature. The reaction mixture was cooled to 10-15° C. and filtered the reaction mixture. Distilled off the solvent completely from the filtrate to get the tile compound.

Yield: 9 gm

Example-14: Preparation of 2-(4-((5,6-diphenylpyrazin-2-yl)(isopropyl)amino)butoxy)acetic acid (Formula-6)

Sodium hydroxide (3.5 gm) was added to a solution of 2-(4-((5,6-diphenylpyrazin-2-yl) (isopropyl) amino) butoxy) acetonitrile (8 gm) in methanol (60 ml) and water (30 ml). The reaction mixture was heated to 65-70° C. and maintained for 6 hrs. The reaction mixture was cooled to 10° C., acidified with diluted hydrochloric acid and stirred at same temperature for 2 hr. The obtained solid was filtered and dried to provide the title compound.

Yield: 7.5 gm

Example-15: Preparation of 2-chloro-N-(methylsulfonyl)acetamide (Formula-16)

The mixture of methane sulfonamide (50 gm) and chloroacetyl chloride (92 gm) was heated to 110-115° C. and stirred the reaction mixture for 7 hours at the same temperature. The reaction mixture was cooled to 25-30° C. and dichloromethane was added to the reaction mixture at the same temperature. Cooled the reaction mixture to 15-20° C. and stirred for 1 hour at the same temperature. Filtered the precipitated solid and washed with dichloromethane. The obtained solid was recrystallized using dichloromethane to get pure title compound.

Yield: 80 gm. M.R.: 110-115° C. Purity by HPLC: 98.85%.

Example-16: Preparation of 4-((5,6-diphenylpyrazin-2-yl)(isopropyl)amino)butan-1-ol (Formula-8)

The mixture of 5-chloro-2,3-diphenylpyrazine (100 gm) and 4-(isopropylamino)butan-1-ol (245.5 gm) was heated to 190-195° C. and stirred the reaction mixture for 12 hours at the same temperature. The reaction was cooled to 25-30° C. and n-heptane was added to the reaction mixture. The reaction mixture was further cooled to 10-15° C., water was slowly added to the reaction mixture and stirred for 2 hours at the same temperature. Filtered the precipitated solid and washed with water. Dichloromethane (300 ml) was added to the obtained solid and stirred for 5 minutes. Both the organic and aqueous layers were separated. The organic layer was dried with sodium sulphate, distilled off the solvent from the organic layer completely under reduced pressure and co-distilled with n-heptane. 400 ml of n-heptane was added to the obtained compound at 25-30° C., heated the reaction mixture to 45-50° C. and stirred for 30 minutes at the same temperature. The reaction mixture was cooled to 15-20° C. and stirred for 2 hours at the same temperature. Filtered the solid, washed with n-heptane and dried to get the title compound.

Yield: 82 gm. M.R.: 100-105° C. Purity by HPLC: 95.4%.

Example-17: Purification of 4-((5,6-diphenylpyrazin-2-yl)(isopropyl)amino)butan-1-ol (Formula-8)

n-Heptane (750 ml) was slowly added to pre-cooled solution of 4-((5,6-diphenylpyrazin-2-yl)(isopropyl)amino) butan-1-ol (100 gm) in acetone (250 ml) was cooled to 0-5° C. Stirred the reaction mixture for 4 hours at the same temperature. Filtered the precipitated solid, washed with n-heptane and dried to get the pure title compound.

Yield: 54 gm. Purity by HPLC: 99.92%.

Example-18: Preparation of Crystalline Form-L of Compound of Formula-1

Figure 10:
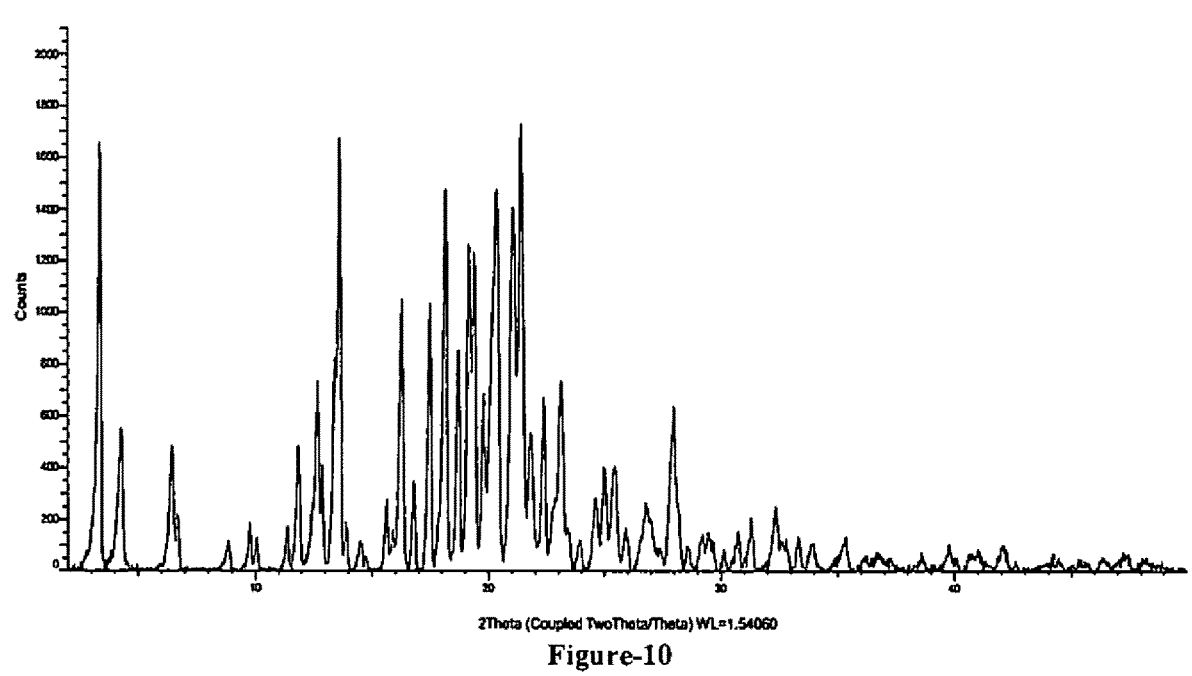
FIG. 10: Illustrates the PXRD pattern of crystalline form-L of 2-{4-[(5,6-diphenylpyrazin-2-yl) (isopropyl) amino]butoxy}-N-(methylsulfonyl) acetamide compound of formula-1.
Figure 11:
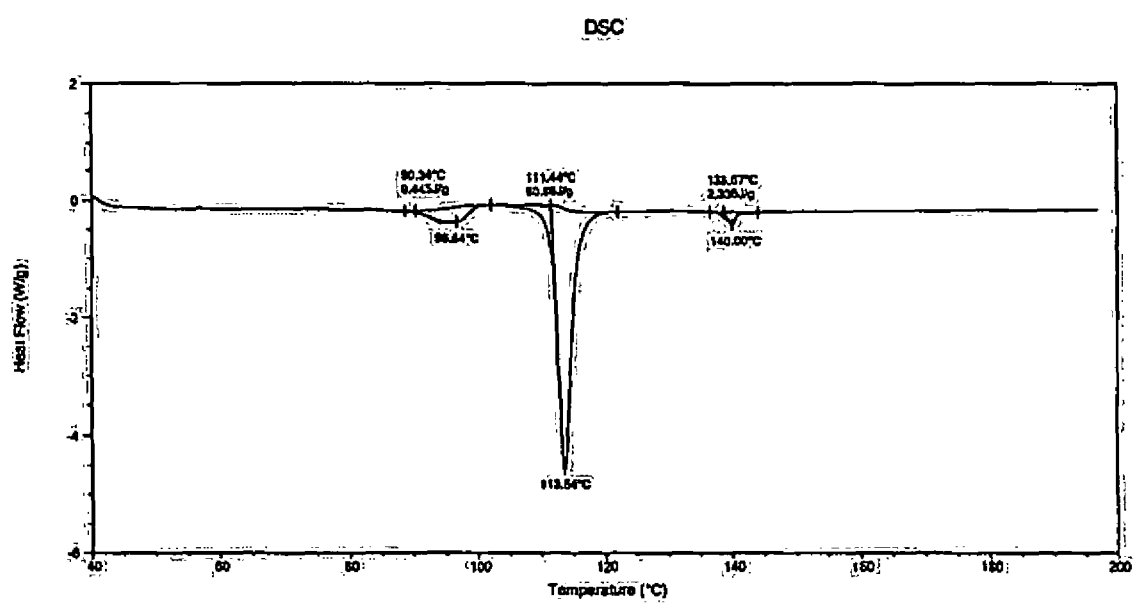
FIG. 11: Illustrates the DSC thermogram of crystalline form-L of 2-{4-[(5,6-diphenylpyrazin-2-yl) (isopropyl) amino]butoxy}-N-(methylsulfonyl) acetamide compound of formula-1.

Melting the compound of formula-1 (10 gm) at 140-145° C. under reduced pressure for 15 minutes. The above obtained oily residue was added to 100 ml of pre-cooled n-heptane at 0-5° C. Stirred the reaction mixture for 6 hr at 0-5° C. Filtered the precipitated solid, washed with n-heptane and dried to get the title compound. Yield: 9 gm; PXRD of the obtained compound is depicted in FIG. 10 and DSC thermogram is depicted in FIG. 11.

Example-19: Preparation of Crystalline Form-P of Compound of Formula-1

Melting the compound of formula-1 (10 gm) at 140-145° C. under reduced pressure for 15 minutes. The above obtained oily residue was added to 100 ml of pre-cooled n-heptane at 0-5° C. Stirred the reaction mixture for 36 hours at 0-5° C. Filtered the precipitated solid, washed with n-heptane and dried to get the title compound.

Figure 7:
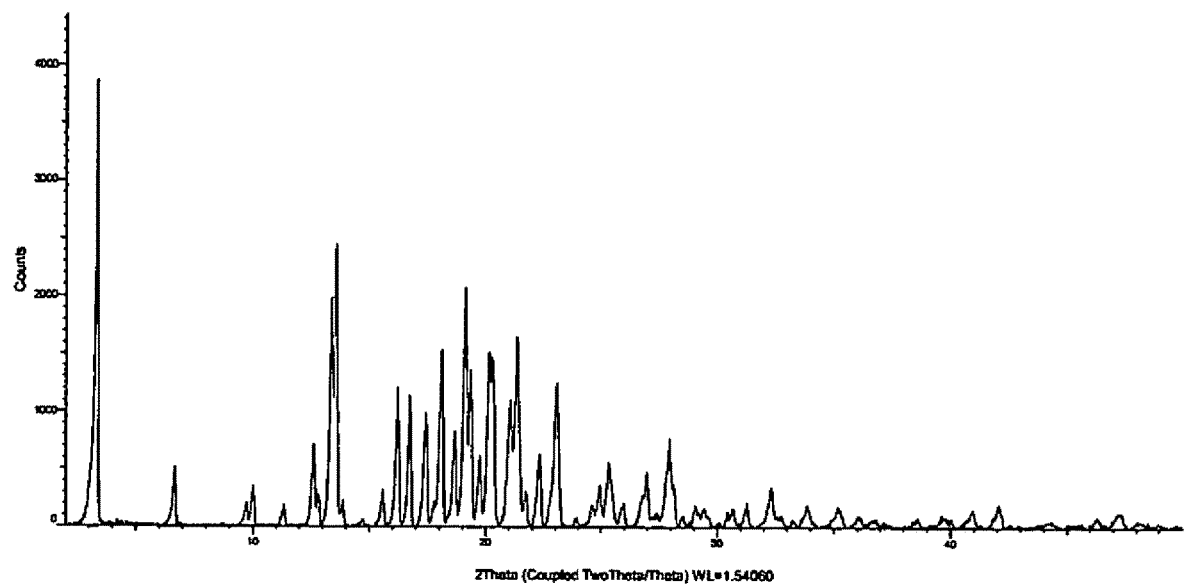
FIG. 7: Illustrates the PXRD pattern of crystalline form-P of 2-{4-[(5,6-diphenylpyrazin-2-yl) (isopropyl) amino]butoxy}-N-(methylsulfonyl) acetamide compound of formula-1.
Figure 8:
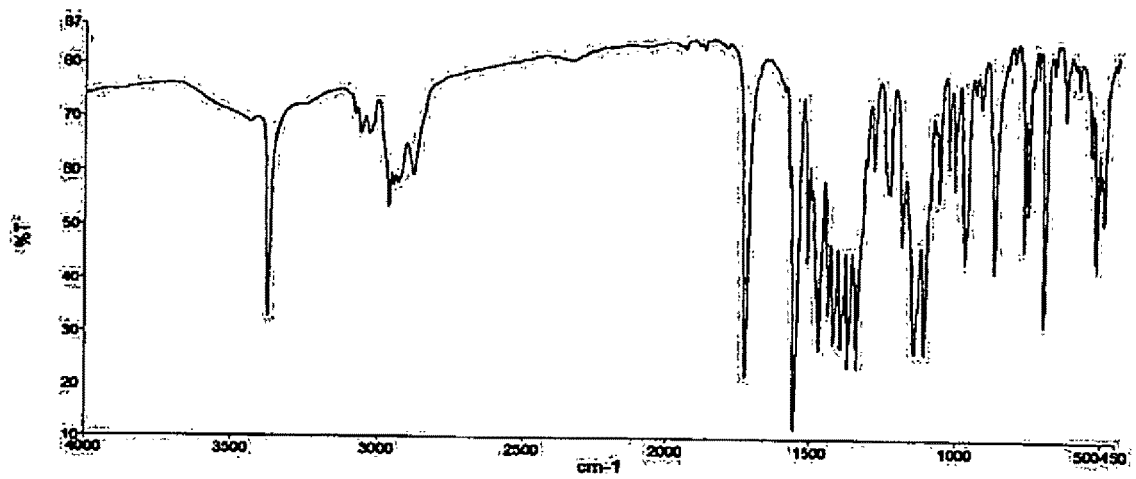
FIG. 8: Illustrates the IR spectrum of crystalline form-P of 2-{4-[(5,6-diphenylpyrazin-2-yl)(isopropyl) amino]butoxy}-N-(methylsulfonyl) acetamide compound of formula-1
Figure 9:
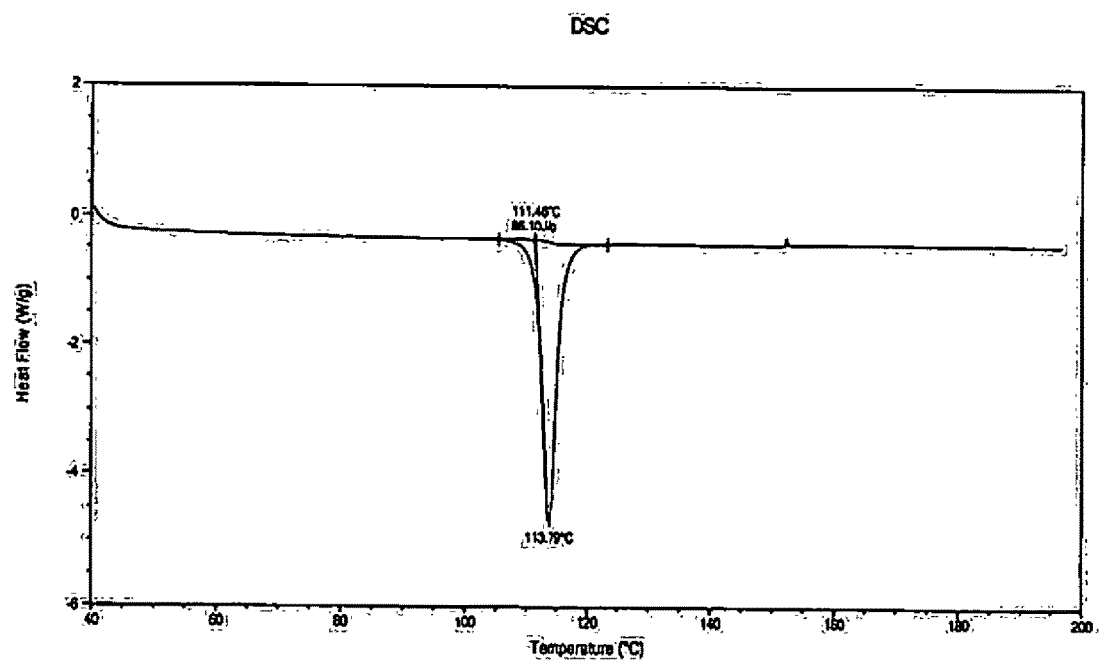
FIG. 9: Illustrates the DSC thermogram of crystalline form-P of 2-{4-[(5,6-diphenylpyrazin-2-yl) (isopropyl) amino]butoxy}-N-(methylsulfonyl) acetamide compound of formula-1.

Yield: 9 gm; PXRD of the obtained compound is depicted in FIG. 7, its IR is depicted in FIG. 8 and its DSC is depicted in FIG. 9.

Example-20: Preparation of Crystalline Form-P of Compound of Formula-1

Melting the compound of formula-1 (10 gm) at 140-145° C. under reduced pressure for 15 minutes. The above obtained oily residue was added to 100 ml of n-heptane at 30-40° C. Stirred the reaction mixture for 36 hours at 30-40° C. Filtered the precipitated solid, washed with n-heptane and dried to get the title compound.

Yield: 9 gm; PXRD of the obtained compound is similar to the FIG. 7.

Example-21: Preparation of Amorphous Form of Compound of Formula-1

Figure 6:
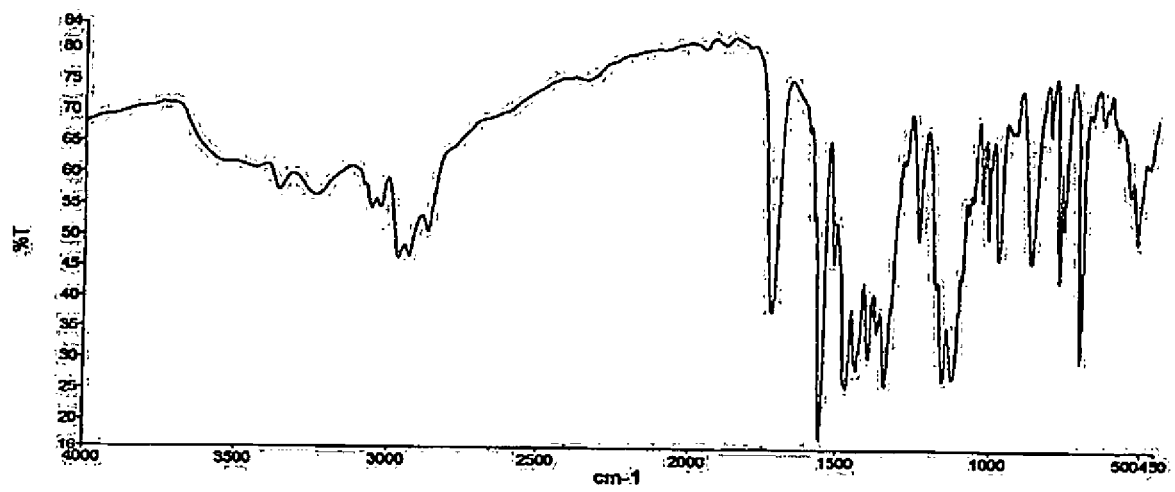
FIG. 6: Illustrates the IR spectrum of amorphous form of 2-{4-[(5,6-diphenylpyrazin-2-yl)(isopropyl) amino]butoxy}-N-(methylsulfonyl) acetamide compound of formula-1.

Melting the compound of formula-1 (10 gm) at 140-145° C. under reduced pressure for 15 minutes and the above obtained oily residue was cooled to 0-5° C. Unload the obtained compound and dried to get the title compound. Yield: 9 gm; Purity by HPLC: 99.74%. PXRD of the obtained compound is depicted in FIG. 5 and IR is depicted in FIG. 6.

Example-22: Preparation of Crystalline Form-I of Compound of Formula-1

Melting the compound of formula-1 (5 gm) at 140-145° C. under reduced pressure for 15 minutes. 50 ml of n-heptane was added to the above obtained oily residue at 115-120° C. Stirred the reaction mixture for 20 minutes at 115-120° C. Cooled the reaction mixture to 25-30° C. and stirred for 60 minutes at the same temperature. Further cooled the reaction mixture to 0-5° C. and stirred the reaction mixture for 60 minutes at the same temperature. Filtered the precipitated solid, washed with n-heptane and dried to get the title compound.

Yield: 4 gm; Purity by HPLC: 99.68%.

Example-23: Preparation of Crystalline Form-P of the Compound of Formula-1

Sodium t-butoxide (40 gm) was added to pre-cooled solution of 4-((5,6-diphenylpyrazin-2-yl)(isopropyl)amino)butan-1-ol (25 gm) in n-methyl pyrrolidone (100 ml) at 0-5° C. and stirred the reaction mixture for 45 min at same temperature. 2-chloro-N-(methylsulfonyl)acetamide (35.5 gm) was slowly added to the reaction mixture at 0-5° C. Raised the temperature of the reaction mixture to 25-30° C. and stirred for 4 hours. The reaction mixture was quenched with pre-cooled water at 0-5° C. and stirred the reaction mixture for 1 hour at the same temperature. Ethyl acetate was added to the reaction mixture and adjusted the pH of the reaction mixture using acetic acid at 0-5° C. The temperature of the reaction mixture was raised to 25-30° C. and separated both the organic and aqueous layers. The aqueous layer was extracted with ethyl acetate and combined the organic layers. The organic layer was washed with aqueous sodium chloride solution and dried the organic layer with sodium sulphate. Distilled off the solvent completely from the organic layer under reduced pressure and co-distilled with n-butanol. Dissolved the obtained compound in n-butanol (220 ml) at 80-85° C. and charcoal (2.5 gm) was added to the reaction mixture at the same temperature and stirred for 30 minutes. Filtered the reaction mixture through hyflow bed and washed with n-butanol. The filtrate was cooled to 25-30° C. and stirred for 3 hours at the same temperature. Filtered the precipitated solid, washed with n-butanol. The obtained compound was recrystallized using n-butanol. Further the obtained compound was recrystallized using the mixture of isopropanol and dichloromethane. The obtained compound was dissolved in the mixture of isopropanol and dichloromethane at reflux temperature. Carbon was added to the reaction mixture and stirred for 1 hour. Filtered the reaction mixture through hyflow bed and washed with isopropanol. The filtrate was cooled to 25-30° C. and stirred for 3 hours at the same temperature. Heating the obtained compound to 160-165° C. under reduced pressure for 15 minutes. The above obtained oily residue was added to 125 ml of pre-cooled n-heptane at 0-5° C. Stirred the reaction mixture for 36 hr at 0-5° C. Filtered the precipitated solid, washed with n-heptane and dried to get the title compound. Yield: 15 gm. PXRD of the obtained compound is similar to the FIG. 7.

Example-24: Preparation of Crystalline Form-P of Compound of Formula-1

Sodium t-butoxide (40 gm) was added to pre-cooled solution of 4-((5,6-diphenylpyrazin-2-yl)(isopropyl)amino)butan-1-ol (25 gm) in n-methyl pyrrolidone (100 ml) at 0-5° C. and stirred the reaction mixture for 45 min at same temperature. 2-chloro-N-(methylsulfonyl)acetamide (35.5 gm) was slowly added to the reaction mixture at 0-5° C. and stirred for 5 hours. The reaction mixture was poured into pre-cooled water at 0-5° C. and stirred the reaction mixture for 1 hour at the same temperature. The reaction mixture was washed with methyl tertiary butyl ether. Acidified the reaction mixture using acetic acid at 0-5° C. The temperature of the reaction mixture was raised to 25-30° C. and separated both the organic and aqueous layers. The aqueous layer was extracted with ethyl acetate and combined the organic layers. The organic layer was washed with aqueous sodium chloride solution and dried the organic layer with sodium sulphate. Distilled off the solvent completely from the organic layer under reduced pressure and co-distilled with methanol. Methanol (1000 ml) was added to the obtained residue at 25-30° C. and stirred for 5 hours at the same temperature. Filtered the precipitated solid and washed with methanol. Dissolved the obtained compound in 1200 ml of methanol at 60-65° C. and filtered the solution through hyflow bed and washed with methanol. Cooled the filtrate to 25-30° C. and stirred for 3 hours at the same temperature. Filtered the precipitated solid and washed with methanol. The obtained wet solid was dissolved in a mixture of ethyl acetate (150 ml) and ethanol (150 ml) at 80-85° C. Charcoal (10 gm) was added to the solution at 80-85° C. and stirred for 10 minutes at the same temperature. Filtered the reaction mixture through hy-flow bed and washed with a mixture of ethanol and ethyl acetate. The filtrate was cooled to 25-35°

C. and stirred for 5 hours at same temperature. Filtered the precipitated solid and washed the mixture of ethyl acetate and ethanol. Heated the obtained compound to 160-165° C. for 15 minutes. The above obtained oily residue was added to 500 ml of pre-cooled n-heptane at 0-5° C. Stirred the reaction mixture for 45 hours at 0-5° C. Filtered the precipitated solid, washed with n-heptane and dried to get the title compound. Yield: 49 gm. Purity by HPLC: 99.76%. PXRD of the obtained compound is illustrated in FIG. 7.

Example-25: Preparation of Compound of Formula-1

Sodium t-butoxide (40 gm) was added to pre-cooled solution of 4-((5,6-diphenylpyrazin-2-yl)(isopropyl)amino) butan-1-ol (25 gm) in n-methyl pyrrolidone (100 ml) at 0-5° C. and stirred the reaction mixture for 45 min at same temperature. 2-chloro-N-(methylsulfonyl)acetamide (35.5 gm) was slowly added to the reaction mixture at 0-5° C. and stirred for 5 hours. The reaction mixture was poured into pre-cooled water at 0-5° C. and stirred the reaction mixture for 1 hour at the same temperature. The reaction mixture was washed with methyl tertiary butyl ether. Acidified the reaction mixture using acetic acid at 0-5° C. The temperature of the reaction mixture was raised to 25-30° C. and separated both the organic and aqueous layers. The aqueous layer was extracted with ethyl acetate and combined the organic layers. The organic layer was washed with aqueous sodium chloride solution and dried the organic layer with sodium sulphate. Distilled off the solvent completely from the organic layer under reduced pressure and co-distilled with methanol. Methanol (1000 ml) was added to the obtained residue at 25-30° C. and stirred for 5 hours at the same temperature. Filtered the precipitated solid and washed with methanol. Dissolved the obtained compound in 1200 ml of methanol at 60-65° C. and filtered the solution through hyflow bed and washed with methanol. Cooled the filtrate to 25-30° C. and stirred for 3 hours at the same temperature. Filtered the precipitated solid and washed with methanol. The obtained wet solid was dissolved in a mixture of ethyl acetate (150 ml) and ethanol (150 ml) at 80-85° C. Charcoal (10 gm) was added to the solution at 80-85° C. and stirred for 10 minutes at the same temperature. Filtered the reaction mixture through hy-flow bed and washed with a mixture of ethanol and ethyl acetate. The filtrate was cooled to 25-35° C. and stirred for 5 hours at same temperature. Filtered the precipitated solid, washed the mixture of ethyl acetate and ethanol and dried to get the title compound.

Yield: 60 gm.

Example-26: Preparation of Crystalline Form-P of Compound of Formula-1

Heated the compound of formula-1 (10 gm) to 160-165° C. for 15 minutes. The above obtained oily residue was added to 100 ml of pre-cooled n-heptane at 0-5° C. Stirred the reaction mixture for 45 hours at 0-5° C. Filtered the precipitated solid, washed with n-heptane and dried to get the title compound.

Yield: 9 gm; PXRD of the obtained compound is illustrated in FIG. 7.

Example-27: Preparation of Crystalline Form-M of Compound of Formula-1

Heated the mixture of the compound of formula-1 (2 gm), ethyl acetate (10 ml) and water (2 ml) to reflux. Stirred the reaction mixture for 20 minutes at the same temperature and filtered the reaction mixture. Distilled off solvent completely from the filtrate under reduced pressure and cooled the obtained compound to 25-30° C. 10 ml of n-heptane was added to the obtained compound at 25-30° C. and stirred it for 45 minutes at the same temperature. Filtered the solid, washed with n-heptane and dried to get the title compound.

Yield: 2 gm; PXRD of the obtained compound is illustrated in FIG. 1.

Example-28: Preparation of Crystalline Form-P of Compound of Formula-1

The mixture of the compound of formula-1 (10 gm) and 100 ml of n-heptane was stirred for 45 hours at 25-35° C. Filtered the solid, washed with n-heptane and dried to get the title compound.

Yield: 9 gm.

Example-29: Preparation of Crystalline Form-D of Compound of Formula-1

Melting the compound of formula-1 (10 gm) at 140-150° C. under reduced pressure for 15 minutes. The above obtained residue was added to 100 ml of pre-cooled n-heptane. Stirred the reaction mixture for 60 minutes at 0-5° C. Filtered the precipitated solid, washed with n-heptane and dried to get the title compound.

Yield: 9 gm; PXRD of the obtained compound is depicted in FIG. 2, DSC is depicted in FIG. 3 and IR is depicted in FIG. 4.

We claim:
1. Crystalline form-P of compound of formula-1

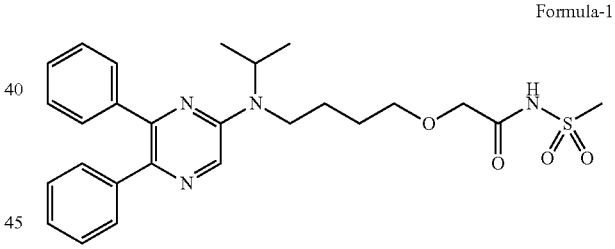

Formula-1 characterized by its powder X-Ray diffraction pattern peaks at about 3.3, 6.6, 13.5±0.2° 2θ.

2. The crystalline form-P of the compound of formula-1 according to claim 1, further characterized by powder X-Ray diffraction pattern having peaks at about 9.7, 12.6, 13.3, 16.2, 17.4, 18.1, 18.6, 19.1, 19.3, 19.7, 20.3, 21.3, 23.0 & 27.9±0.2° 2θ.

3. The crystalline form-P of the compound of formula-1 according to claim 1, further characterized by its PXRD pattern shown in FIG. 7.

4. The crystalline form-P of the compound of formula-1 according to claim 1, further characterized by its DSC histogram shown in FIG. 9.

5. The crystalline form-P of the compound of formula-1 according to claim 1, further characterized by its IR spectrum shown in FIG. 8.

6. A process for the preparation of crystalline form-P of compound of formula-1 according to claim 1, comprising:
   a) heating the compound of formula-1 to a suitable temperature, b) combining the obtained compound in step-a) with the solvent at a suitable temperature,
c) stirring the reaction mixture for more than 24 hours at a suitable temperature,
d) filtering the obtained solid in step-c) to provide crystalline form-P of compound of formula-1.

7. The process according to claim 6, wherein the suitable temperature in step a) is 90 to 180° C.

8. A process for the preparation of the crystalline form-P of compound of formula-1 according to claim 1, comprising:
a) heating the compound of formula-1 to 140-170° C.,
b) adding the obtained compound in step-a) to pre-cooled n-heptane at 0-10° C.,
c) stirring the reaction mixture for 30-50 hours at below 30° C.,
d) filtering the obtained solid in step-c) to provide the crystalline form-P of compound of formula-1.

9. The crystalline form-P of compound of formula-1 obtained according to claim 6 having purity >95% by HPLC.

10. The crystalline form-P of compound of formula-1 obtained according to claim 6 having particle size of D(0.9) <200 μm.

11. A process for the preparation of a pharmaceutical composition comprising use of crystalline form-P of compound of formula-1 of claim 1.

12. A pharmaceutical composition comprising crystalline form-P of compound of formula-1 according to claim 1 and a pharmaceutically acceptable carrier.

13. A method of treating arteriosclerosis pulmonary hypertension or Raynaud's disease secondary to systemic sclerosis in a subject, comprising administering a pharmaceutical composition comprising crystalline form-P of compound of formula-1 of claim 1 to the subject.

14. The process according to claim 6, wherein the suitable temperature in step-a) is 135 to 145° C. under reduced pressure.

15. The process according to claim 6, wherein the solvent in step b) is a single solvent or mixture of solvents and is selected from hydrocarbon solvents, ester solvents, chloro solvents, ketone solvents.

16. The process according to claim 15, wherein the solvent is hydrocarbon solvent.

17. The process according to claim 16, wherein the hydrocarbon solvent is n-heptane.

18. The process according to claim 6, wherein the suitable temperature in step c) is below 40° C.

* * * * *